(12) United States Patent
Dhawan et al.

(10) Patent No.: US 6,703,045 B2
(45) Date of Patent: Mar. 9, 2004

(54) COMPOSITION AND METHOD FOR MAINTAINING BLOOD GLUCOSE LEVEL

(75) Inventors: Sanju Dhawan, Chandigarh (IN); Anil Kumar Singla, Chandigarh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/935,057

(22) Filed: Aug. 21, 2001

(65) Prior Publication Data

US 2003/0113371 A1 Jun. 19, 2003

(51) Int. Cl.[7] .................................................. A61K 9/20
(52) U.S. Cl. ..................... 424/464; 424/465; 424/484; 424/486; 424/488; 424/468; 424/451; 424/452; 424/457; 514/772; 514/772.1
(58) Field of Search ................................ 424/484, 486, 424/488, 464, 465, 468, 451, 452, 457; 514/772, 772.1

(56) References Cited

U.S. PATENT DOCUMENTS

| | | |
|---|---|---|
| 4,346,709 A | 8/1982 | Schmitt |
| 4,696,815 A | 9/1987 | Schepky et al. |
| 4,803,076 A | 2/1989 | Ranade |
| 5,024,843 A | 6/1991 | Kuczynski et al. |
| 5,091,190 A | 2/1992 | Kuczynski et al. |
| 5,100,669 A | 3/1992 | Hyon et al. |
| 5,512,297 A | 4/1996 | Baichwal et al. |
| 5,945,125 A * | 8/1999 | Kim .......................... 424/473 |
| 6,245,357 B1 | 6/2001 | Edgren et al. |
| 6,270,797 B1 * | 8/2001 | Gidwani et al. ............ 424/457 |
| 6,348,469 B1 * | 2/2002 | Seth ........................... 514/255 |

OTHER PUBLICATIONS

Clark, Charles M. and Vincor, Frank; "Introduction: Risks and Benefits of Intensive Management in Non–Insulin–Dependent Diabetes Mellitus," Annals of Internal Medicine, vol. 124, No. 1 (Part 2), pp. 81–85, Jan. 1, 1996.

Porte, Daniel and Schwarz, Michael W.; "Diabetes Complications: Why is Glucose Potentially Toxic?," Science, vol. 272, pp. 699–700, May 3, 1996.

(List continued on next page.)

Primary Examiner—Thurman K. Page
Assistant Examiner—Charesse Evans
(74) Attorney, Agent, or Firm—Oliff & Berridge, PLC

(57) ABSTRACT

A composition useful for reducing serum glucose levels by an oral controlled release system and a method for treating diabetes in a human being by controlling the blood glucose level (BGL) and reducing the complications associated with diabetic hyperglycemia and also the long term management of Non-Insulin Dependent Diabetes Mellitus (NIDDM) by avoiding the problems associated with the tight control of BGL, i.e., hypoglycemia tolerance and seizures. The composition is directed to a solid, hydrophilic matrix controlled release oral dosage form where the dosage form contains a therapeutically effective amount of antidiabetic drug in the matrix ensuring complete bioavailability of the drug from the matrix of the tablet. The formulation undergoes substantially or approaches zero order release of active drug and the concentration of the excepients and the water swellable polymers is chosen in such a way that the erosion or dissolution rate of the polymer is equal to the swelling rate of the polymer to get a constant release. Also, the concentration is chosen in such a way that the tablet will be fully dissolved at the same time the last of the drug is released and in addition a bioadhesive polymer may also be added to increase the residence time of the dosage form in the g.i.t. and at high concentration of the polymer, beta cyclodextrin may also be added to improve the release kinetics.

11 Claims, 4 Drawing Sheets

OTHER PUBLICATIONS

Ishii, Hidehiro et al.; "Amelioration of Vascular Dysfunctions in Diabetic Rats by an Oral PKC B Blocker," Science, vol. 272, pp. 728–731, May 3, 1996.

UKPDS Group, UK Prospective Diabetes Study Group, "Intensive Blood–Glucose Control with Sulphonylureas or Insulin Compared with Conventional Treatmetn and Risk of Complications in Patients with Type 2 Diabetis (UKPDS 33)," The Lancet, vol. 352, pp. 837 thru 853, Sep 12, 1998.

"Tight Control for Type 2 Diabetes," HealthNews, vol. 10, p. 5, Oct. 15, 1998.

Boyle, P.J. et al.; "Brain Glucose Uptake and Unawareness of Hypoglycemia in Patients with Insulin–Dependent Diabetes Mellitus," The New England Journal of Medicine, vol. 332, No. 26, pp. 1726–1731, Dec. 28, 1995.

The Diabetis Control and Complications Trial Research Group; The Effect of Intensive Treatment of Diabetes on the Development and Progression of Long–Term Complications in Insulin–Dependent Diabetes Mellitus, The New England Journal of Medicine, vol. 329, No. 14, pp. 977–985, Sep. 30, 1993.

American Diabetes Association; "Implications of the Diabetes Control and Complications Trial," Diabetes Care, vol. 6, No. 4, pp. 1 thru 6, (1993).

Miller, J.L. et al.; "Bedtime Insulin Added to Daytime Sulfonylureas Improves Glycemic Control in Uncontrolled Type II Diabetes," Clinical Trials and Theraputics, vol. 53, pp. 380–384, Mar., 1993.

Shank, Myron L. et al.; "Bedtime Insulin/Daytime Glipizide–Effective Therapy for Sulfonylurea Failures in Niddm," Diabetes, vol. 44, No. 2, pp. 165–172, Feb., 1995.

Lebovitz, Harold E.; "Glipizide: A Second–Generation Sulfonylurea Hypoglycemic Agent," Pharmcotherapy, vol. 5, No. 2, pp. 63–77, Mar./Apr., 1985.

Lebovitz, Harold E.; "Oral Sulfonylurea Hypoglycemic Drugs," Pharmacy Times, vol. 51, pp. 108–116, Oct., 1985.

Editors, J.E.F. Reynolds; "Martindale, The Extra Pharmacopocia," 13th Edition, pp. 347–348, The Pharmaceutical Press, London, (1993).

"AHFS Drug Information," pp. 755, (1989).

Brogden, R.N. et al.; "Glipizide: A Review of Its Pharmacological Properties and Theraputic Use," Drugs, vol. 18, pp. 329–353, (1979).

www.pfizer.com/hml/pi's/glucotrolxlpi.pdf, pp. 1 thru 14.

Kradjan, Wayne A. et al.; "Pharmacokinetics and Pharmacodynamics of Glipizide After Once–Daily and Divided Doses," Pharmacotherapy, vol. 15, No. 4, pp. 465–471, (1995).

Berelowitz, M. et al.; "Comparative Efficacy of Once Daily Controlled–Release Formulation of Glipizide and Immediate–Release Glipizide in Patients with NIDDM," Diabetis Care, vol. 17, No. 12, pp. 1460–1464, (1994).

Riddle, Matthew C. et al.; "Glipizide–Gits Does Not Increase the Hypoglycemic Effect of Mile Exercise During Fasting in NIDDM," Diabetis Care, vol. 20, No. 6, pp. 992–994, (1997).

Blonde, L. et al.; "The Glipizide Gits Efficacy and Safety Trial Study Group. Glipizide Gits is Effective and Safe in a Wide Range of NIDDM Patients: Results of a Double Blind, Placebo Controlled Efficacy and Safety Trial," Diabetes, vol. 45, Suppl. 2, pp. 285A, (1996).

British Pharmacopoeia, vol. II, pp. 1 thru 3, The Stationery Office, London, (1999).

United States Pharmacopeia, XXIII National Formulary 18, United States Pharmacopeial Convention, Inc., Rockvill, Maryland, pp. 707–708, (1995).

FDA; "Guidance for Industry: Dissolution Testing of Immediate Released Dosage Forms," Cover Page, Index, pp. 1 thru 11, Appendix pp. 1 & 2, Bibliography, Aug., 1997.

Amidon, Gordon L. et al.; A Theoretical Basis for a Biopharmaceutic Drug Classification: The Correlation of In Vitro Drug Product Dissolution and In Vivo Bioavailability, Pharmaceutical Research, vol. 12, No. 3, pp. 413–420, (1995).

Guidance for Industry, "Glipizide: In Vivo Bioequivalence and In Vitro Dissolution Testing," pp. 1 thru 11, Office of Generic Drugs, 7500 Standish Place, Metro Park North, Rockville, Maryland, No Date Available.

United States Pharmacopeia, XXIII National Formulary 18, United States Pharmacopeial Convention, Inc., Rockville, Maryland, Supplement One, pp. 2465, (1995).

Shenfield, Gillian M. et al.; "A Screening Test for Detecting Sulfonylureas in Plasma," Therapeutic Drug Monitoring, vol. 12, pp. 393–397, (1990).

FDA; "Guidance for Industry: Supac–Mr: Modified Relese Solid Oral Dosage Forms." Cover Page, Index, i & ii, pp. 1 thru 23, errata page, Sep., 1997.

Shah, Vinod P. et al.; "in Vitro Dissolution Profile Comparison–Statistics and Analysis of the Similarity Fact, F2," Pharmaceutical Research, vol. 15, No. 6, pp. 889–896, (1998).

Tang, Y. and Gan, K.; "Statistical Evaluation of In Vitro Dissolution of Different Brands of Ciprofloxacin Hydrochloride Tablets and Capsules," Drug Development and Industrial Pharmacy, vol. 24, No. 6, pp. 549–552, (1998).

FDA; "Guidance for Industry: Bioavailability and Bioequivalence Studies for Orally Administered Drug Products—General Considerations," Cover Page, Index, i & ii, pp. 1 thru 21, appendix pp. 1 & 2, Oct., 2000.

Bottenberg, P. et al.; "Development and Testing of Bioadhesive, Fluoride–Containing Slow–Release Tablets for Oral Use," Journal of Pharmacology, vol. 43, pp. 457–464, (1991).

"Polyox Water Soluble Resins, NF in Sustained–Releaase Oral Pharmaceutical Applications," pp. 1 thru 8, Sentry Polyox, Danbury, Conn. (No Date).

Gupta, Alka et al.; "Measuement of Bioadhesive Strength of Mucoadhesive Buccal Tablets: Design of an In–Vitro Assembly," Indian Drugs, vol. 30, No. 4, pp. 152–155, (1993).

Ritger, Philip L. et al.; "A Simple Equation for Description of Solute Release II. Fickian and Anomalous Release from Swellable Devices," Journal of Controlled Release, vol. 5, pp. 37–42, (1987).

Khar, Roop K. et al.; "Mucoadhesive Drug Delivery," Department of Pharmaceutics, Faculty of Pharmacy, Jamia Hamdard, New Delhi, India, pp. 353 thru 380 (No Date).

Ch'ng, Hung Seng et al.; "Bioadhesive Polymers as Platforms for Oral Controlled Drug Delivery II: Synthesis and Evaluation of Some Swelling, Water–Insoluble Bioadhesive Polymers," Journal of Pharmaceutical Sciences, vol. 74, No. 4, pp. 399–405, Apr., 1985.

Leung, Sau–Hung S. et al.; "Polymer Structure Features Contributing to Mucoadhesion. II.," Journal of Controlled Release, vol. 12, pp. 187–194, (1990).

Anderson, N.H. et al.; "Evaluation of Fit Factors and Dissolution Efficiency for the Comparison of In Vitro Dissolution Profiles," Journal of Pharmaceutical and Biomedical Analysis, vol. 17, pp. 811–822, (1998).

Polli, James E. et al.; "Methods to Compare Dissolution Profiles and a Rationale for Wide Dissolution Specifications for Metoprolol Tartrate Tablets," Journal of Pharmaceutical Sciences, vol. 36, No. 6, pp. 690 thru 700, Jun., 1997.

"Sentry Polyox WSR, A Mucoadhesive Drug Delivery Vehicle," pp. 1 thru 6, Sentry Polyox, Danbury, Conn. (No Date).

Novoseven–me//D./patients/ming/gnpizide3.mm, pp. 1–5, Nationwide Survey Finds Patients May Mistake Medication Side Effects for Symptoms of Type 2 Deabetes, NOVO Nordisk, (No Date).

* cited by examiner

COMPOSITION AND METHOD FOR MAINTAINING BLOOD GLUCOSE LEVEL

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A COMPUTER PROGRAM APPENDIX

Not Applicable

INCORPORATION BY REFERENCE

The following publications which are identified herein using a number inside parenthesis (e.g., (1)) are hereby incorporated by reference:

(1) American Diabetes Association. Diabetes 1996 Vital Statistics. Rockville, Md.: American Diabetes Association, 1996.
(2) Harris, M. I., Cowie, C. C., Stern, M. P. eds. Diabetes in America, 2nd. ed. National Institutes of Health. National Institute of Diabetes and Digestive and Kidney Diseases. *NIH Publication No.* 95-1468, 1995.
(3) Clark, C. M., Vinicor, F. Introduction: Risks and benefits of intensive management in non-insulin-dependent diabetes mellitus. The Fifth Regensrief Conference. *Ann Intern Med*, 124(1, pt 2), 81–85, 1996.
(4) Porte, J. and Schwartz, M. W., Diabetes complications: Why is glucose potentially toxic?, *Science*, 272, 699–700, 1996.
(5) Ishii, H., Jirousek, M. R., Koya, D., Takagi, C., Xia, P., Clermont, A., Bursell, S. E., Kern, T. S., Ballas, L. M., Heath, W. F., Stramm, L. E., Feener, E. P. and King, G. L., Amelioration of vascular dysfunctions in diabetic rats by an oral PKC βinhibitor, *Science*, 272, 728–731, 1996.
(6) UKPDS Group. UK Prospective Diabetes Study 33: Intensive blood-glucose control with sulphonylureas or insulin compared with conventional treatment and risk of complications in patients with type 2 diabetes. *Lancet*, 352, 837–853, 1998.
(7) Incidence and risk factors for serious hypoglycemia in older persons using insulin or sulfonylurea. *Arch Int Med*, 8, 25, 1997.
(8) Tight control for type 2 diabetes. *Health News*, 10, 25, 1998.
(9) Boyle, P. J., Kempers, S. F., O'Connor, A. M. and Nagy, R. J., Brain glucose uptake and unawareness of hypoglycemia in patients with insulin-dependent diabetes mellitus, *New Eng J. Med* 333(26), 1726–1731, 1995.
(10) Diabetes Control and Complications Trial Research Group. The effect of intensive treatment of diabetes on the development and progression of long-term complications in insulin-dependent diabetes mellitus. *N Engl J Med*, 329, 977–986, 1993.
(11) American Diabetes Association. Implications of the Diabetes Control and Complications Trial. *Diabetes Spec* 6(4), 225–227, 1993.
(12) Lewin, D. I., Brain's adaptation to low blood sugar endangers diabetics, *J. NIH Research*, 8, 38–39, 1996.
(13) Miller, J. L., Salman, K., Shulman, L. H. and Rose, L. I., Bed time insulin added to daytime sulfonylurea improves glycemic control in uncontrolled type II diabetes, *Clin. Pharmacol. Ther.*, 53 (Mar), 380–384, 1993.
(14) Shank, M. L., Prato, S. D. and DeFronzo, R. A., Bedtime insulin/daytime glipizide, effective therapy for sulfonylurea failures in NIDDM, *Diabetes*, 44(2), 165–172, 1995.
(15) Labovitz, H. E., Glipizide : A second generation sulfonylurea hypoglycaemic agent, *Pharmcotherapy*, 5 (2), 63–77, 1985.
(16) Labovitz, H. E., Oral sulfonylurea hypoglycemic drugs, *Pharmacy Times*, 51, 108–116, 1985.
(17) Martindale, The Extra Pharmacopoeia, Thirtieth Edition, Eds. J. E. F. Reynolds, The Pharmaceutical Press, London, 1993.
(18) AHFS Drug Information, 1989, pp 1741–1745.
(19) Brogden, R. N., Heel, R. C., Pakes, G. E., Speight, T. M. and Avery, G. S., Glipizide : A review of its pharmacological properties and therapeutic use, *Drugs*, 18, 329–353, 1979.
(20) www.pfizer.com/hml/pi':s/glucotrolxlpi.pdf.
(21) Peterson, C. M., Sims, R. V., Jones, R. L. and Rieders, F., Bioavailability of glipizide and its effect on blood glucose and insulin levels in patients with non-insulin-dependent diabetes, *Diabetes care*, 5, 497–500, 1982.
(22) Feinglos, M. N. and Lebovitz, H. E., Long term safety and efficacy of glipizide, *Am. J. Med.*, 25 (suppl. 5B), 60–66, 1983.
(23) Kradjan, W. A., Takeuchi, K. Y., Opheim, K. E. and Wood, F. C. Pharmacokinetics and pharmacodynamics of glipizide after once-daily and divided doses, *Pharmacotherapy*, 15 (4), 465–471, 1995.
(24) Berelowitz, M., Fischette, C., Cefalu, W., Schade, D. S., Sutfin, T., and Kourides, I. A., Comparative efficacy of once daily controlled-release formulation of glipizide and immediate-release glipizide in patients with NIDDM, *Diabetes Care*, 17 (12), 1460–1464, 1994.
(25) Riddle, M. C., Mcdaniel, P. A. and Tive, L. A., Glipizide-GITS does not increase the hypoglycemic effect of mild exercise during fasting in NIDDM, *Diabetes Care*, 20 (6), 992–994, 1997.
(26) Blonde, L., Guthrie, R. D., Tive, L., Fischette, C. The Glipizide GITS efficacy and safety trial study group. Glipizide GITS is effective and safe in a wide range of NIDDM patients: results of a double blind, placebo controlled efficacy and safety trial, *Diabetes* 45 (suppl. 2): 285A, 1996.
(27) British Pharmacopoeia, London The Stationery Office, Volume II, pp1862, 1999,.
(28) United States Pharmacopeia XXIII National Formulary, 18, United States Pharmacopeial Convention Inc. Rockville, pp707–708, 1995.
(29) Lachman, Leon, Liberman, H. A. and Kanig, J. L., The theory and Practice of Industrial Pharmacy, Varghese Publishing House, Bombay,1991.
(30) Guidance for Industry: Dissolution testing of immediate released dosage forms. FDA, August 1997.
(31) Amidon, G. L., Lennernas, H., Shah, V. P. and Crison, J. R. A., Theoretical basis for a biopharmaceutic drug classification: the correlation of In vitro drug product dissolution and in vivobioavailability, Pharm. Res., 12, 413–420, 1995.
(32) United States Pharmacopeial Convention, Inc., July 1998, In vitro-In vivo Correlation for extended release oral dosage forms, Pharmacopeial Forum Stimuli Article, 4160–4161.
(33) Guidance for Industry, Glipizide, In vivobioequivalence and In vitro dissolution testing, Division of

(34) United States Pharmacopeia XXIII National Formulary, 18, United States Pharmacopeial Convention Inc. Rockville, Supplement I pp2465, 1995.
(35) Shenfield, G. M., Boutagy, J. S. and Webb, C. A screening test for detecting sulfonylureas in plasma, *Therapeutic Drug Monitoring*, 1990, 12, 393–397.
(36) Guidance for Industry: SUPAC-MR: modified release solid oral dosage forms scale-up and postapproval changes: chemistry, manufacturing, and controls; In vitro dissolution testing and In vivobioequivalence documentation.FDA, September 1997.
(37) Shah, V. P., Tsong, Y., Sathe, P. and Liu, J. P., In vitro dissolution profile comparison-statistics and analysis of the similarity factor, $f_2$, *Pharm. Res.* 15, 889–896, 1998.
(38) Tang, Y. and Gan, K., Statistical evaluation of In vitro dissolution of different brands of ciprofloxacin hydrochloride tablets and capsules, *Drug. Dev. Ind. Pharm.*, 24(6), 549–552, 1998.
(39) Guidance for Industry: Bioavailability and bioequivalence studies for orally administered drug products—General considerations.
(40) Hunt, G., Kearney, P. and Kellaway, I. W., Mucoadhesive polymers in drug delivery systems, in *Drug Delivery Systems* (Eds P. Johnson and J. G. Lloyd-Jones), Ellis Horwood Ltd. Chichester, UK, and VHC Verlagsgesellschaft GmbH Weinheim, Germany, pp.180–199, 1987.
(41) Sau-Hung, Leugand, S. and Robinson, J. R., Bioadhesives in drug delivery, *Polym. News* 15, 333, 1990.
(42) Chen,m J. L. and Cyr, G. N., Composition producing adhesion through hydration, in Adhesion in Biological systems (Ed. R. S. Manly), Academic Press, new York and London, ch. 10, pp. 163–167, 1970,
(43) P. Bottenberg et al., Development and testing of bioadhesive fluoride containing slow release tablets for oral use, *J. Pharm. Pharmacol.*, 43,457–464, 1991.
(44) Polyox Water soluble resins, NF in sustained—Release Oral pharmaceutical applications, Union Carbide, Danbury Conn., Literature#UC377.
(45) Gupta, A., Garg, S. and Khar, A. K., Measurement of bioadhesive strength of mucoadhesive buccal tablets: Design of an In vitro assembly, *Indian Drugs*, 30, 152–155, 1993.
(46) Martin, F., Physical Pharmacy, Fourth Edition, Lea and Febiger, Philadelphia, London, 305–330.
(47) Ritger, P. L. and Peppas, N. A., 1987b, A simple equation for description of solute release II. Fickian and anamolous release from swellable devices. *Journal of Controlled Release*, 5, 37–42.

The following U.S. Pat. Nos. are incorporated herein by reference:

4,346,709 August, 1982 Schmitt 128/260
4,696,815 September, 1987 Schepky et al. 424/80
4,803,076 February, 1989 Ranade 424/438
5,024,843 June, 1991 Kuczynski et al. 424/499
5,091,190 February, 1992 Kuczynski et al
5,100,669 March, 1992 Hyon et al. 424/426
5,512,297 April, 1996 Baichwal 424/451
6,245,357 June, 2001, Edgren, et. al 1. Field of the Invention The present invention relates to a composition useful for reducing serum glucose levels by an oral controlled release system. Also, the invention describes a method of reducing serum glucose levels by an oral controlled release dosage form incorporating glipizide and the dosage form administered once a day will provide therapeutic levels of the drug throughout the day.

2. Background of the Invention

Diabetes mellitus (DM) is a complex chronic disorder of carbohydrate, fat, and protein metabolism that results primarily either from a partial or complete lack of insulin secretion by the beta cells of the pancreas or from defects in cellular insulin receptors.

The two primary types of Diabetes Mellitus can be described based on the level of insulin production by the person's pancreatic beta cells:

Type I Diabetes (IDDM)—Little or no insulin is produced as the pancreatic beta cells have been destroyed by the body's own immune system. Type I Diabetes is also known as Insulin Dependent Diabetes Mellitus (IDDM) since the individual is dependent on daily insulin injections for his survival. Between 5–10% of all diabetics are IDDM (Ref.:1; —American Diabetes Association. Diabetes 1996 Vital Statistics. Rockville, Md.: American Diabetes Association, 1996.)

Type II Diabetes (NIDDM)—Pancreatic beta cells produce insulin but not in sufficient quantities to maintain healthy blood glucose levels. Non-Insulin Dependent Diabetes Mellitus (NIDDM) results from the deterioration in the molecular machinery that mediates the effectiveness of insulin function on cells (e.g. insulin resistance and inadequate insulin secretion). Between 90–95% of all diabetics are NIDDM (Ref.: 2—Harris, M. I., Cowie, C. C., Stern, M. P. eds. Diabetes in America, 2nd. ed. National Institutes of Health. National Institute of Diabetes and Digestive and Kidney Diseases. *NIH Publication No.* 95–1468, 1995).

The pathological complications of diabetes are fundamentally related to hyperglycemia. For example, it appears that hyperglycemia can induce increased aldose reductase activity which affects sorbitol accumulation, depletes neural myoinositol, and alters Na—K ATPase activity. Hyperglycemia also increases diacylglycerol and $\beta_2$ protein kinase C activity, which in turn alters the contractility and hormone responsiveness of vascular smooth muscle, and alters endothelial cell permeability. Moreover, hyperglycemia is associated with accelerated non-enzymatic glycosylation processes which activate endothelial and macrophage receptors for advanced glycosylation endproducts (AGEs), and alters lipoproteins as well as matrix and basement membrane proteins. It is clear that the consequences of glucose toxicity are globally distributed throughout the physiology of the diabetic patient.

If the diabetes is poorly controlled it can lead to diabetic complications. Diabetic complications are much more common in type 2 patients with approximately 50% suffering from one or more complications at the time of diagnosis (Ref.:3—Clark, C. M., Vinicor, F. Introduction: Risks and benefits of intensive management in non-insulin-dependent diabetes mellitus. The Fifth Regensrief Conference. *Ann Intern Med,* 124(1, pt 2), 81–85, 1996.).

Diabetic complications can be split into two main categories:

Microvascular

Macrovascular

Diabetes affects the small blood vessels throughout the body. Damage to these vessels and the basement membrane causes impaired delivery of nutrients and hormones to the tissues, resulting in tissue damage. The sites most affected are the retina, renal glomerulus and the nerve sheath.

Retinopathy

This is a major cause of blindness in diabetic patients. Microangiopathy affecting the retina develops over a number of years. Vision is not affected by all retinopathies, however prompt treatment is necessary in controlling the condition and maintaining vision.

Nephropathy

This is a major cause of mortality in diabetics. Diabetic nephropathy is recognized by the detection of albuminuria from urine tests. Progress is evaluated by measuring albumin excretion (microalbuminuria=30–300 mg/24 hr; macroalbuminuria>300 mg/24 hr) from a timed urine collection.

Neuropathy

Diabetic neuropathy affects the sensory nerve system causing pain (sharp, stabbing or burning particularly on the shins and soles of feet). Other symptoms of autonomic neuropathy include impotence in men, gastrointestinal dysfunction and lack of sweating in the feet.

Macrovascular Complications

This affects the larger vessels in the body and is more likely in type 2 diabetes patients. The complications of high blood glucose levels both in the short and long term are what make diabetes a frightening disease (Ref.: 4—Porte, J. and Schwartz, M. W., Diabetes complications: Why is glucose potentially toxic?, *Science*, 272, 699–700, 1996). The most common acute symptoms (thirst, frequent urination, fatigue and weight loss) can be explained by how the body attempts to deal with the high levels of sugar in the blood system. When sugar levels are high blood begins to thicken. This signals the body to consume fluids (thirst). The kidneys monitor fluid levels and removes the excess fluids through urination (frequent urination). When sugar levels are elevated, sugars spill into the urine and energy and calories are lost (fatigue and weight loss). Numerous years of high or uncontrolled BGL produce severe long term complications. Diabetes is a result of a fundamental problem—the body is unable to process sugar into energy correctly. Over time this fundamental problem affects many areas of a person's body making diabetes "The Department Store of Disease". Long term problems of diabetes include:

Long-Term Complications of Diabetes

Injuries in large blood vessels endanger the heart, particularly in people with existing heart disease or high blood pressure.

Cardiovascular Complications

Heart attacks account for 60% and strokes for 25% of deaths in all diabetics. A recent study reported that people with type 2 diabetes and no history of a heart disease have the same seven-year risk for a heart attack as nondiabetics with heart disease. Both type 1 and 2 diabetes accelerate the progression of atherosclerosis, a process whereby layers of yellowish plaque made up of cholesterol, fats, and other particles build up in the walls of arteries. As the arteries narrow, blood flow slows and the blood vessels may become blocked. This can lead to coronary artery disease, heart attack, or stroke. Type 2 diabetes are more likely than the general population to have high triglyceride levels and lower high density lipoprotein (HDL)—both risk factors for heart disease. Insulin resistance is also often accompanied by high blood pressure, another major cause of heart attack, stroke, and heart failure (ref.:-5: Ishii, H., Jirousek, M. R., Koya, D., Takagi, C., Xia, P., Clermont, A., Bursell, S. E., Kern, T. S., Ballas, L. M., Heath, W. F., Stramm, L. E., Feener, E. P. and King, G. L., Amelioration of vascular dysfunctions in diabetic rats by an oral PKC βinhibitor, *Science*, 272, 728–731, 1996).

Mental Function and Dementia

Studies indicate that patients with type 2 diabetes face a higher than average risk of developing dementia caused either by Alzheimer's disease or problems in blood vessels in the brain. Problems in attention and memory can occur even in people under 55 who have had diabetes for a number of years.

Other Complications

People with diabetes are at higher risk for influenza and its complications, including pneumonia, possibly because the disorder neutralizes the effects of protective proteins on the surface of the lungs. Women with type 2 diabetes face a higher risk for uterine cancer although only if they are obese. Both women and men with diabetes appear to have a higher risk for colon and rectal cancers.

Complications in Pregnancy

Both preexisting diabetes in pregnant women and temporary diabetes that occurs during pregnancy (gestational diabetes) can increase the risk for birth defects. Because glucose crosses the placenta, a woman with diabetes can pass high levels of blood glucose to the fetus. In response, the fetus secretes large amounts of insulin. This combination of high fetal blood levels of insulin and glucose leads to excessive fetal growth. It may also contribute to delayed maturation of the lungs or to the death of the fetus.

Hypoglycemia

Intensive insulin or treatments that produce insulin, such as sulfonylureas, increase the risk of hypoglycemia (or insulin shock), which occurs if blood glucose levels fall below normal (Ref.: 6—UKPDS Group. UK Prospective Diabetes Study 33: Intensive blood-glucose control with sulphonylureas or insulin compared with conventional treatment and risk of complications in patients with type 2 diabetes. *Lancet*, 352, 837–853, 1998). Hypoglycemia may also be caused by insufficient intake of food, exercise, or alcohol intake. Usually the condition is manageable, but occasionally, it can be severe or even life threatening, particularly if the patient fails to recognize the symptoms (refs:-7,8—Incidence and risk factors for serious hypoglycemia in older persons using insulin or sulfonylurea. *Arch Int Med*, 8, 25, 1997. Tight control for type 2 diabetes. *HealthNews*, 10, 25, 1998). Mild symptoms usually occur at moderately low and easily correctable levels of blood glucose; they include sweating, trembling, hunger, and rapid heartbeat. Severely low blood glucose levels can precipitate neurologic symptoms—confusion, weakness, disorientation, combativeness, and in rare and worst cases, coma, seizure, and death. Patients who experience repeated episodes of hypoglycemia may become insensitive to symptoms; even a single recent episode of hypoglycemia may make it more difficult to detect the next episode. By rigorously avoiding low blood glucose, such patients can regain the ability to sense the symptoms. Experts have been concerned that the increased incidence of hypoglycemia accompanying strict blood glucose control could cause mental deterioration over time. This observation is attributed to the unusual and interesting feature of the brain that, while like other organs systems in its reliance on blood glucose concentration for function, the brain differs from other organs in that it does not need insulin to utilize glucose. Boyle et al. (1995) (9) have reported that hypoglycemia is likely to lead to a reversible, maladaptive central nervous system tolerance to subnormal plasma glucose concentrations. Specifically, certain autonomic portions of the brain adapt physiologically, learning to tolerate low blood glucose levels. By contrast, the rest of the brain, and in particular the cognitive portions, do not possess this capacity. Defective glucose counterregulation can occur even after only a single episode of hypoglycemia. Patients who experience repeated episodes of hypoglycemia often lose their capacity to recognize the symptoms typically associated with hypoglycemia or impending insulin shock, a condition called "hypoglycemia unawareness." Because the patient doesn't appreciate his or her own status, blood glucose levels can then fall so low that serious neurological problems ensue, including coma and seizure.

The Diabetes Control and Complications Trial (DCCT) (10), a ten-year study completed in mid-1993, demonstrated that tight or "intensive" control of blood glucose levels—i.e., frequent self-monitoring of glucose levels and maintenance of these levels as close as possible to those in nondiabetics-significantly reduces diabetes-associated complications, such as retinopathy, nephropathy and neuropathy. The DCCT (11) showed that the frequency of health complications was 40–75% lower for persons in the intensive control group than for those in the conventional treatment group. It has since become a central doctrine of diabetic management that the intensive control of hyperglycemia is critical to effective retardation or delay in the appearance or progression of the late complications of the disease. However, it was found in the DCCT that patients in the intensive treatment group more often suffered from seizures or coma or required another person's assistance to recover from hypoglycemia than did patients treated less intensively. The chief adverse complication associated with intensive therapy was 3-fold increase in the incidence of severe hypoglycemia, defined as the need for assistance from others, as compared to diabetics undertaking conventional therapy. Thus, the danger in maintaining artificially a patient's blood glucose within the narrow, normal range-the essence of intensive control prescribed according to the DCCT—is that such regimens can induce recurrent low blood-glucose levels, raising the threat of seizure or a coma with little or no warning. Lewin in 1996(12) has recognized that tight control of the blood glucose levels poses a difficult dilemma. Specifically, while tight control of blood glucose levels appears to be required to control hyperglycemia-associated pathology, in practice the patient often overcorrects, thereby inducing repeated episodes of hypoglycemia, giving rise to hypoglycemia unawareness. In order to provide a long term solution to Type II sufferers, a comprehensive treatment must be provided to assist them in maintaining healthy or near normal blood sugar levels. Boyle et al. have also found that, because the body, and especially the brain, adapts to lower blood sugar levels, there is little margin between the blood glucose level at which hypoglycemic signs become perceptible and the level at which dangerous cognitive impairment occurs. Accordingly, patients who use rigorous treatment regimens to maintain near-normal plasma glucose levels are at increased risk for seizures and comas. It is difficult to achieve the tightest level of glycemic control (to minimize microvascular and other complications) while at the same time avoiding even a slight degree of hypoglycemia (to avoid central nervous system tolerance to subnormal glucose levels). Thus, there is a clear need for additional understanding of these interrelated physiological processes, as well as for new diabetes treatment regimens that avoid the problems that have so far plagued effective patient management.

Drug

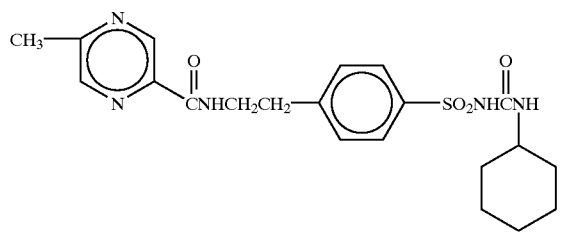

Glipizide(1-cyclohexyl-3-[[p-[2-(5-methylpyrazinecarboxamido)ethyl]phenyl]sulfonyl]urea), a second generation sulfonylurea is effective in controlling the blood glucose in patients with NIDDM (13–16).

Glipizide is a whitish odorless powder with a $pK_a$ 5.0 and is insoluble in water and alcohols but soluble in 0.1N NaOH (17,18). DOSE : There is no fixed dosage regimen for the management of diabetes mellitus with glipizide or any other hypoglycemic agent. In addition to the usual monitoring of urinary glucose, the patient's blood glucose must also be monitored periodically to determine the minimum effective dose for the patient; to detect primary failure, i.e., inadequate lowering of blood glucose at the maximum recommended dose of medication; and to detect secondary failure, i.e., loss of an adequate blood-glucose-lowering response after an initial period of effectiveness. Glycosylated hemoglobin levels may also be of value in monitoring the patient's response to therapy.

Short-term administration of glipizide may be sufficient during periods of transient loss of control in patients usually controlled well on diet. As with other sulfonylurea-class hypoglycemics, many stable non-insulin-dependent diabetic patients receiving insulin may be safely placed on glipizide. Dosage may be adjusted at intervals of several days by amounts of 2.5 to 5 mg daily to a maximum of 40 mg daily.

Pharmacokinetics

Glipizide is completely absorbed and peak plasma conc. varying between 380 to 611 ng/ml (0.85 to 1.35 mmol/ml) are attained usually 1–3 hr after a single oral 5 mg dose. Plasma concentrations decline to 12.0 ng/ml after 24 hr. The apparent volume of distribution of glipizide in man has been reported to be 11.5 to 25 liters and that of central compartment 6 to 10 liters. It is extensively bound to human serum proteins. Glipizide is almost completely metabolized and the metabolites are devoid of hypoglycaemic activity. The principal metabolites of the glipizide are the 4-trans-hydroxycylcohexyl derivative, the 3-cis-hydroxycyclohexyl derivative, and N-(2-acetylamino-ethyl phenyl-sulphonyl)-N' cyclohexyl urea (19).

Half life : It has a half life of approximately 2–4 hr.

Mechanism Of Action of Controlled Release Tablets

Glipizide appears to lower blood glucose acutely by (i) Insulin release from pancreatic β cells: This effect is dependent upon functioning beta cells in the pancreatic islets. It binds to ATP-sensitive potassium channel on the beta cell membrane. Binding of this sulfonylurea inhibits the efflux of potassium ion through the channel and results in depolarization which in turn opens a calcium channel and results in calcium influx and release of preformed insulin.

(ii) Reduction of serum glucagon concentration: Chronic administration of sulfonylurea to NIDDM patients reduces serum glucagon levels which contributes to the hypoglycemic effects of the drug.

(iii) Potentiation of insulin action on the target tissues: Increased binding of insulin to tissue receptor occurs during in vivo sulfonylurea administration.

Effects on Blood Glucose

The effectiveness of glipizide extended-release tablets in NIDDM at doses from 5–60 mg once daily has been evaluated in 4 therapeutic clinical trials each with long-term open extensions involving a total 598 patients. Once daily administration of 5, 10, and 20 mg produced statistically significant reductions from placebo in hemoglobin $A_1c$, fasting plasma glucose and postprandial glucose in mild to severe NIDDM patients. In a pooled analysis of the patients treated with 5 mg and 20 mg, the relationship between dose and glipizide extended-release's effect of reducing hemoglobin $A_1c$ was not established. However, in the case of fasting plasma glucose patients treated with 20 mg had a statistically significant reduction of fasting plasma glucose compared to the 5 mg-treated group.

The reductions in hemoglobin $A_1c$ and fasting plasma glucose were similar in younger and older patients. Efficacy of glipizide extended-release was not affected by gender, race, or weight (as assessed by body mass index). In long term extension trials, efficacy of glipizide extended-release was maintained in 81% of patients for up to 12 months.

In an open, two-way crossover study 132 patients were randomly assigned to either glipizide extended-release or glipizide for 8 weeks and then crossed over to the other drug for an additional 8 weeks. Glipizide extended-release administration resulted in significantly lower fasting plasma glucose levels and equivalent hemoglobin $A_1c$ levels, as compared to glipizide (20).

Pharmacokinetics and Metabolism

Glipizide is rapidly and completely absorbed following oral administration in an immediate release dosage form. The absolute bioavailability of glipizide was 100% after single doses in patients with NIDDM. Beginning 2 to 3 hours after administration of glipizide extended-release tablets, plasma drug concentrations gradually rise reaching maximum concentrations within 6 to 12 hours after dosing. With subsequent once daily dosing of glipizide extended-release tablets, effective plasma glipizide concentrations are maintained throughout the 24 hour dosing interval with less peak to through fluctuation than that observed with twice daily dosing of immediate release glipizide. The mean relative bioavailability of glipizide in 21 males with NIDDM after administration of 20 mg glipizide extended-release tablets, compared to immediate release glipizide (10 mg given twice daily), was 90% at steady state. Steady state plasma concentrations were achieved by at least the fifth day of dosing with glipizide extended-release tablets in 21 male with NIDDM and patients younger than 65 years. Approximately 1 to 2 days longer were required to reach steady state in 24 elderly (>65 years) males and females with NIDDM. No accumulation of drug was observed in patients with NIDDM during chronic dosing with glipizide extended-release tablets. Administration of glipizide extended-release with food has no effect on the 2 to 3 hour lag time in drug absorption. In a single dose, food effect study in 21 healthy males subjects, the administration of glipizide extended-release immediately before a high fat breakfast resulted in a 40% increase in the glipizide mean $C_{max}$ value, which was significant, but the effect on the AUC was not significant. There was no change in glucose response between the fed and fasting state. Markedly reduced GI retention times of the glipizide extended-release tablets over prolonged periods (e.g., short bowel syndrome) may influence the pharmacokinetic profile of the drug and potentially result in lower plasma concentrations. In a multiple dose study in 26 males with NIDDM, the pharmacokinetics of glipizide were linear over the dose range of 5 to 60 mg of glipizide extended-release in that the plasma drug concentrations increased proportionately with dose. In a single dose study in 24 healthy subjects, four 5 mg, two 10 mg, and one 20 mg glipizide extended-release tablets were bioequivalent(20).

In patients with NIDDM, the drug has a much greater effect in potentiating meal induced insulin secretion (21,22). Glipizide is an exception among all sulfonylureas, whose ability to potentiate nutrient stimulated insulin secretion persists during long term therapy while with other drugs, this effect is lost after 6–12 months of therapy. It has been shown that glipizide-GITS (an extended release tablet for oral use) is more effective than immediate release glipizide in reducing fasting plasma glucose levels (23). Both formulations reduce postprandial plasma glucose levels equally, however glipizide-GITS exerts its control in the presence of lower plasma glipizide concentrations in addition to significantly lower insulin and c-peptide levels. This suggests that glipizide-GITS improves insulin sensitivity. Studies have proved that chronic use of extended-release glipizide does not enhance the hypoglycemic effect of fasting plus mild exercise for people with NIDDM (24–26). It is clear that the controlled release preparations of glipizide have shown better efficacy than immediate release dosage.

Contraindications

Immediate and Extended Release Tablets

Glipizide is Contraindicated in Patients with Known Hypersensitivity to the Drug Diabetic ketoacidosis, with or without coma. This condition should be treated with insulin.

Drug Interactions

The hypoglycemic action of sulfonylureas may be potentiated by certain drugs including nonsteroidal anti-inflammatory agents and other drugs that are highly protein bound, salicylates, sulfonamides, chloramphenicol, probenecid, coumarins, monoamine oxidase inhibitors, and beta adrenergic blocking agents. When such drugs are administered to a patient receiving glipizide, the patient should be observed closely for hypoglycemia. When such drugs are withdrawn from a patient receiving glipizide, the patient should be observed closely for loss of control. In vitro binding studies with human serum proteins indicate that glipizide binds differently than tolbutamide and does not interact with salicylate or dicumarol. However, caution must be exercised in extrapolating these findings to the clinical situation and in the use of glipizide with these drugs.

Certain drugs tend to produce hyperglycemia and may lead to loss of control. These drugs include the thiazides and other diuretics, corticosteroids, phenothiazines, thyroid products, estrogens, oral contraceptives, phenytoin, nicotinic acid, sympathomimetics, calcium channel blocking drugs, and isoniazid. When such drugs are administered to a patient receiving glipizide, the patient should be closely observed for loss of control. When such drugs are withdrawn from a patient receiving glipizide, the patient should be observed closely for hypoglycemia.

A potential interaction between oral miconazole and oral hypoglycemic agents leading to severe hypoglycemia has been reported. Whether this interaction also occurs with the intravenous, topical, or vaginal preparations of miconazole is not known.

The effect of concomitant administration of fluconazole and glipizide has been demonstrated in a placebo-controlled crossover study in normal volunteers. All subjects received glipizide alone and following treatment with 100 mg of fluconazole as a single daily oral dose for 7 days. The mean percentage increase in the glipizide AUC after fluconazole administration was 56.9% (range: 35 to 81).

Adverse Effects

Gastrointestinal

Gastrointestinal disturbances are the most common reactions. Gastrointestinal complaints were reported with the following approximate incidence: nausea and diarrhea, one in seventy; constipation and gastralgia, one in one hundred. They appear to be dose-related and may disappear on division or reduction of dosage. Cholestatic jaundice may occur rarely with sulfonylureas, glipizide should be discontinued if this occurs.

Dermatologic

Allergic skin reactions including erythema, morbilliform or maculopapular eruptions, urticaria, pruritus, and eczema have been reported in about one in seventy patients. These may be transient and may disappear despite continued use of glipizide; if skin reactions persist, the drug should be discontinued. Porphyria cutanea tarda and photosensitivity reactions have been reported with sulfonylureas.

Miscellaneous

Dizziness, drowsiness, and headache have each been reported in about one in fifty patients treated with glipizide. They are usually transient and seldom require discontinuance of therapy.

Disadvantages of the Known Formulations

Glipizide does not accumulate in the plasma following repeated oral dosing. Glipizide tablets are available, e.g., in 5 and 10 mg immediate release formulations and extended release dosage forms Glucotrol XL 5 mg, 10 mg and 20 mg (Pfizer Inc. USA) and Glytop SR 5 mg (Sidmak Laboratories (India) Ltd)

Immediate release tablets formulated with a sulfonylurea based on an acidified and/or alkalized excipient and an inert polar solvent, such as polyethylene glycol, are described by U.S. Pat. No. 4,696,815. These pH regulated, immediate release formulations are described as improving the dissolution of acidic, amphoteric or basic antidiabetic sulfonylurea compounds, respectively. For example, the alkalized excipient is said to promote improved dissolution of glipizide, which is an acid compound. An analogous immediate release formulation with an acidified and/or alkalized excipient, an inert polar solvent and polyvinylpyrrolidone is also described by U.S. Pat. No. 4,696,815.

Erodible poly(orthoester) or poly(orthocarbonate) devices for implantation or insertion into a patient are described by U.S. Pat. No. 4,346,709, for delivering a drug in a controlled manner, including oral hypoglycemic drugs such as the sulfonylurea hypoglycemics, acetohexamide, glypinamide, chlorpropamide, tolazamide, tolbutamide, phenformin.

A controlled release delivery system using melt spun biodegradable polymers as a carrier or host material for a bio-effecting agent such as a pharmaceutical active or a hormonal compound, including glipizide, for e.g., oral administration, is described by U.S. Pat. No. 5,518,730.

Controlled release microspheres for administration by, e.g., the oral route and comprising polylactic acid and a water soluble physiologically active substance and having a mean particle size of from about 0.01 $\mu$m to 300 $\mu$m are described by U.S. Pat. No. 5,100,669 as including active substances such as the antidiabetic agents glipizide, glymidine sodium, phenformin hydrochloride, methformin, buformin hydrochloride.

Uniformity and predictability of therapeutic levels of sulfonylureas and resulting blood sugar levels are considered to be desirable in the management of diabetic patients, and in particular, for the management of type II diabetic patients. For example, in tests with art-known extended release glipizide (formulations based on orally ingestible osmotic devices, as discussed herein below) it has been shown that fasting plasma glucose levels were significantly lower in patients treated with controlled release glipizide than with immediate-release glipizide.

Extended release sulfonylurea formulations with improved dissolution properties, and particularly, extended release formulations of second generation sulfonylureas, are therefore a desirable addition to the medical treatment of diabetes, including type II diabetes. Of these second generation drugs, efforts to provide controlled release have focused on glipizide. Art-known extended release glipizide formulations are available as osmotic based dosage forms, such as, for example, Glucotrol XL Extended Release TabletRTM (Pratt Pharmaceuticals; 5 to 60 mg unit doses). As with other art-known extended release glipizide, discussed hereinbelow, Glucotrol XLRTM is prepared as an osmotic pump formulation. Specifically, Glucotrol XL.RTM is prepared as an osmotically active drug core surrounded by a semipermeable membrane. The core itself is divided into two layers: an "active" layer containing the drug, and a "push" layer containing pharmacologically inert (but osmotically active) components. The membrane surrounding the tablet is permeable to water but not to drug or osmotic excipients. As water from the gastrointestinal tract enters the osmotically active material, the tablet pressure increases in the osmotic layer and "pushes" against the drug layer, resulting in the release of drug through a small laser-drilled orifice in the membrane on the drug side of the tablet.

Other osmotic pump devices and formulations for administering glipizide are described in U.S. Pat. Nos. 5,091,190 and 5,024,843 (Kucrynski et al.) and in U.S. Pat. No. 4,803,076 (Gautman). These patents describe the delivery of glipizide in a controlled manner by the use of an oral formulation based on another osmotic pump design. U.S. Pat. No. 4,792,448 (Gautman) has also described the zero order release of glipizide using a device described as a strip covered by an impermeable wall with uncovered areas.

U.S. Pat. No. 6,245,3576 teaches a controlled release dosage form comprising an osmotic core, an interior wall, said interior wall comprises a hydrophobic substance and a hydrophilic substance and a fluid permeable exterior wall surrounding the interior wall. However, this system is restricted to analgesic compositions only. In addition, this combination is for delivering higher quantities of drugs and not suitable for releasing lower quantities of drugs, which are required in certain kinds of physiological conditions such as diabetes II. In case of diabetes II, the drug release should not be more than 40% of the drug at a time. In case, if the drug is released more, then it triggers sudden lowering of serum glucose level, which in turn cause adverse effects and complications to the patient. Therefore, there is a need to construct a slow and controlled release drug delivery system. The present invention meets the above requirement by providing a oral controlled release system for diabetes II.

All of these formulations, therefore, are prepared from a plurality of osmotic pump devices that require complex manufacturing processes with attendant high costs. Moreover in osmotic pumps, the amount of drug added is more than the dose of the drug in order to achieve a constant release. This may lead to increase in cost in case of costly drugs.

Therefore, there has not previously been a fully satisfactory and economical formulation for providing a predictable and uniform treatment regimen, which avoids the need for the construction of complex devices for oral administration and that have the further advantage of simplifying treatment and improving patient compliance while both enhancing the bioavailability of the antidiabetic drug and prolonging the release of the drug. A significant problem facing the pharmaceutical formulator attempting to prepare a bioavailable oral sustained release dosage form of a sulfonylurea relates to the ability of the dosage form to release the drug over the desired period of time to such an extent that the sulfonylurea content of the dosage form will be effectively bioavailable. One aspect of this problem is the fact that sulfonylureas are relatively insoluble and therefore inherently difficult to be solubilized from an oral dosage form in the gastrointestinal tract and then be absorbed through the walls of the gastrointestinal tract. This solubility and bioavailability problem has been overcome with respect to immediate release oral sulfonylurea dosage form by utilizing a solubilizing agent, as discussed above. However, such agents are expected to cause the fast, i.e., immediate, release of all of the sulfonylurea when orally administered. Therefore, the use of such solubilizing agents would not necessarily be considered desirable in sustained release oral dosage forms, where the goal is to slow the release of drug from the dosage form over an extended period of time. Thus, there is a continuing need in the art for a relatively simple and economical controlled release sulfonylurea formulation for oral administration that is fully bioavailable and suitable for administration once every 24 hours.

BRIEF SUMMARY OF THE INVENTION

The present invention provides a composition useful for reducing serum glucose levels by an oral controlled release system The present invention is directed to an improved and more economical method for the stable and convenient treatment of diabetes of the type II that is responsive to control by a sulfonylurea antidiabetic agent. Also the present invention is directed to a method for preparing a bioavailable controlled release 24 hour formulation for antidiabetic drugs such as sulfonylurea, glipizide drugs.

Accordingly, the present invention relates to a composition useful for reducing serum glucose levels by an oral controlled release system and a method for treating diabetes in a human being by controlling the blood glucose level (BGL) and reducing the complications associated with diabetic hyperglycemia and also the long term management of Non-Insulin Dependent Diabetes Mellitus (NIDDM) by avoiding the problems associated with the tight control of BGL, i.e., hypoglycemia tolerance and seizures. The invention is directed to a novel, solid, hydrophilic matrix controlled release oral dosage form where the dosage form contains a therapeutically effective amount of antidiabetic drug in the matrix ensuring complete bioavailability of the drug from the matrix of the tablet and the formulation undergoes substantially or approaches zero order release of active drug and the concentration of the excepients and the water swellable polymers is chosen in such a way that the erosion or dissolution rate of the polymer is equal to the swelling rate of the polymer to get a constant release. Also, the concentration is chosen in such a way that the tablet will be fully dissolved at the same time the last of the drug is released and in addition a bioadhesive polymer may also be added to increase the residence time of the dosage form in the g.i.t. and at high concentration of the polymer, beta cyclodextrin may also be added to improve the release kinetics.

An object of this invention is to provide a dosage form for delivering glipizide in a rate controlled amount, and which dosage form substantially overcomes the hypoglycemia associated with the tight control of blood glucose levels.

One of the main objects of the invention is to provide a composition for reducing glucose serum levels by oral controlled release system.

Another object of the invention is to provide a regimen to achieve near normal blood glucose levels in the patient, with a low incidence of undesirable side effects for the therapy.

Still another object of the present invention is to reduce the risk of long term damage to organs and tissues resulting from sustained hyperglycemia.

Still another object of the present invention is to enable the patient to maintain as near normal a lifestyle as possible while ensuring adequate control of his or her diabetes.

Yet another object of the present invention is to provide a dosage form for orally administering glipizide in a rate-controlled dose for blood-glucose lowering therapy.

Yet another object of the invention is to provide a method for treating hyperglycemia by orally administering glipizide in a rate-controlled dose per unit time to a human being in need of hyperglycemia therapy.

One more objects of the invention is to provide a pharmaceutical dosage form that makes available controlled and sustained glipizide therapeutic activity to a patient in need of glipizide therapy.

Another object of the invention is to provide a novel dosage form manufactured as hydrophilic, swellable and erodible device that can administer glipizide to a biological receptor site to produce the desired glipizide pharmacological effects.

Another object of the present invention is to provide a dosage form that can deliver the substantially aqueous insoluble drug glipizide at a controlled and beneficial known rate over time.

Another object of the present invention is to provide a complete pharmaceutical glipizide regimen comprising a composition comprising glipizide that can be dispensed from a drug delivery dosage form, the use of which requires intervention only for initiation and possibly for termination of the regimen.

It is also an object of the invention to provide oral anti-diabetic glipizide pharmaceutical compositions.

It is a further object of the invention to provide a process for preparing said glipizide compositions.

Another object of the invention is to provide a dosage form comprising the drug N-[2-[4-[[[(cyclohexylamino) carbonyl]-amino]sulfonyl]phenyl]ethyl]-5-methyl pyrazinecarboxamide and a pharmaceutically acceptable carrier that forms and provides a dispensable composition when the dosage form is delivering the drug to the patient.

It is also an object of the invention to provide a novel and economical controlled release dosage formulation of glipizide.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
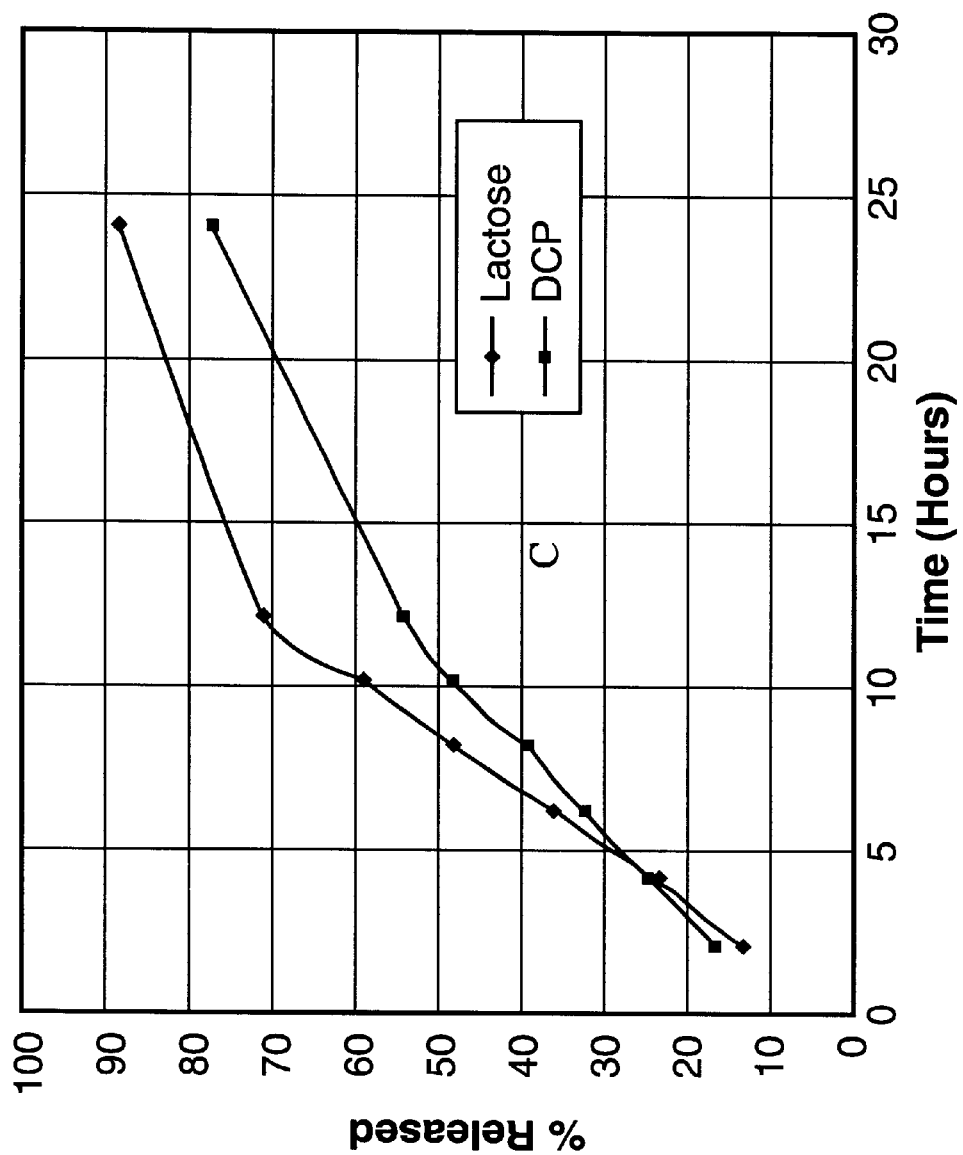
FIG. 1 is a graph showing the effect of diluents on the release of glipizide.

Accordingly the present invention provides a composition for reducing serum glucose levels having an oral controlled release system, said composition comprising:
 i. a medicament;
 ii. one or more water soluble, high viscosity, bioadhesieve polymer for slow release of medicament; and
 iii. optionally pharmaceutically acceptable additive.

In an embodimant of the present invention, the said polymer used in the composition is an hydrophilic and water swellable polymer and also having bioadhesieve properties.

In another embodiment of the invention relates to the medicament which, is an antidiabetic selected from group consisting essentially of sulphonylurea and glipizide.

In still another embodiment of the invention, wherein the polymer is selected from the group consisting of poly(ethylene oxide), hydroxypropylmethylcellulose, carboxypolymethylene (carbopol) and mixtures thereof.

In yet another embodiment of the invention, the polyethylene oxide is selected from the group comprising polyethylene oxides having molecular weight ranging from 4,000,000 to 8,000,000.

In yet another embodiment of the invention, the hydroxypropylmethylcellulose is selected from group comprising hydroxypropylmethylcellulose having a viscosity ranging rom 4,000 to 21,000 cps.

In yet another embodiment of the invention, the pharmaceutically acceptable additives consisting of one or more lubricants and diluents selected from the group comprising magnesium stearate, stearic acid, talc, dicalcium phosphate, lactose and microcrystalline cellulose.

Yet another embodiment of the present invention the lubricant is selelcted from the group comprising magnesium stearate, stearic acid and talc.

Yet another embodiment of the present invention the diluent is selelcted from the group comprising dicalcium phosphate, lactose and microcrystalline cellulose In yet another embodiment of the invention, the medicament and optionally pharmaceutically acceptable additives are in the form of a core which is encapsulated with the water soluble, high viscosity, bioadhesieve polymer.

In yet another embodimen of the invention, the composition is in the form of tablet or capsule.

One more embodiment of the invention relates to a composition for reducing serum glucose levels by an oral controlled release system, said composition comprising polythene oxide 10–40% by weight, drug 5–10%, an pharmaceutically acceptable additive 0 to 5% and dicalcium Phosphate q.s.

In another embodiment of the invention relates to once a day controlled release tablet for reducing serum glucose level and for treating hyperglycemia, said tablet comprising:
 i. a medicament;
 ii. one or more water soluble, high viscosity, bioadhesieve polymers for slow release of medicaments; and
 iii. optionally pharmaceutically acceptable additive.

In another embodiment of the invetion wherein, the pharmaceutically acceptable additive comprising a lubricant and a diluent, the medicament is an antidiabetic drug selected from sulphonylurea, glipizide and, the polymer is hydrophilic and water swellable.

Yet another embodiment of the invention, the polymer used in the once a day controlled release tablet for reducing the serum glucose level and treating the mammals, is selected from the group consisting of poly(ethylene oxide), hydroxypropylmethylcellulose, carboxypolymethylene (carbopol) and mixtures thereof.

Yet another embodiment of the invention relates to the lubricant which is selected from magnesium stearate, stearic acid and talc and the diluent selected from dicalcium phosphate, lactose and microcrystalline cellulose.

One more embodiment of the invention relates to a method of reducing a patient's serum glucose level, said method comprising administering to the patient orally a therapeutically effective amount of controlled release medicament encapsulated with water soluble, high viscosity, bioadhesieve polymer, and the said medicament is delivered to the patient's circulatory system at a continual rate over a period of several hours.

Another embodiment of the present invention relates to a method for treating hyperglycemia in a patient, wherein the method comprises administering to the patient a dosage form comprising 2 mg to 50 mg glipizide , which is administered at a therapeutical dose effective over 24 hours from the dosage form comprising one or more hydrogel selected from the group consisting of poly(ethylene oxide) having a 4,000,000 to 8,000,000 molecular weight and a hydroxy propylmethylcellulose (viscosity 4000 to 21000 cps) and carboxypolymethylene (carbopol 934P) to the patient to produce the intended effect.

In another embodiment of the present invention relates to a process for producing a pharmaceutical composition used for treating mammals, said process comprising a core made of medicament and optionally one or more pharmaceutically acceptable additive, encapsulated with water soluble, high viscosity, bioadhesieve polymer.

In accordance to the present invention provides a controlled release tablet including a pharmaceutical agent glipizide and an excipient. The excipient includes at least about 5–80% of a mixture of water swellable polymers and a lubricant. The water swellable polymer is chosen such that the swelling rate of the polymer is equal to the dissolution rate of the swollen polymer. The lubricant is generally present in an amount of up to 3% of the excipient as a whole. The excipient may also include such other ingredients as diluents, fillers, binders and other pharmacologically inactive compounds. Further, the polymer and pharmaceutical agent are complementary. In selecting a water swellable polymer, the polymer should be chosen with the pharmaceutical agent in mind such that the tablet will be fully dissolved at the same time that the last of the pharmaceutical agent is released so that the whole of the drug may be made bioavailable.

The second necessary characteristic of the formulation is that it does not release all of the active ingredient at one time but rather releases the active ingredient gradually over time. This is particularly important because
 (1) glipizide has a relatively short half life and
 (2) a desired level of glipizide in blood serum must be maintained over a long period to obtain the desired effect.

If all of the glipizide is released at once it will all enter the circulatory system at once and be metabolized in the liver thereby causing the drug serum level to drop below the desired level. When this occurs the effect on reducing glucose levels is suboptimal.

In summary, it will be appreciated that the present invention contributes to the art an unexpected and unforseen dosage form that possesses the practical utility for administering aqueous insoluble glipizide from hydrphilic matrix dosage form. While the invention has been described and pointed out in detail with reference to operative embodiments thereof it will be understood that those skilled in the art that various changes, modifications, substitutions and omissions can be made without departing from the spirit of the invention.

Formulation in General

Monolithic systems, composed of hydrophobic polymers and other excipients, are commonly used for extended release dosage forms because they are not costly or difficult to produce. However, such systems often provide a square-root-of-time kinetics (i.e. the amount of pharmaceutical agent released is proportional to the square root of the time since the drug was ingested). There are several ways to improve the release kinetics of extended release dosage forms. Incorporation of hydrophilic polymers into monolithic matrices modifies square root kinetics due to the swelling of the polymer. In particular, monolithic matrix systems controlled by the swelling/erosion processes of hydrophilic polymers can improve the pharmaceutical agent release kinetics. However, even in these systems, the release rate of the pharmaceutical agent generally varies significantly with time.

Hydrophilic polymers alone have also been investigated for controlled drug release. The hydrophilic polymers such as hydroxypropylmethyl cellulose (HPMC) and polyvinylalcohol (PVA), which form gels upon contact with water and erode slowly, have been utilized for oral drug delivery systems.

The excipients of the present invention have been formulated to allow controlled release of glipizide. The excipients of the present invention generally comprise a hydrophilic polymer and a lubricant. Other pharmacologically inactive materials also can be added. Polyethylene glycol and cyclodextrins are generally used to increase the solubility of relatively insoluble drugs to encourage absorption by the body. Other solubilizers may also be used. The polymers set forth herein may be compressed into tablets directly. Optionally, binders, fillers, or other typical compounding agents may be added to adjust the properties of the final tablets. Particularly, but without limitation, the following compounds may be included: lactose, dextrose, sucrose, and calcium phosphate. Specifically, the polymeric materials useful in the present invention will depend to a certain extent on the amount of glipizide chosen to be administered. Polymers of choice include uncrosslinked polyethylene oxide (PEO) and hydroxypropylmethylcellulose (HPMC) both of varying molecular weight and viscosity, respectively. HPMC is available on the basis of viscosity measured in a 2% solution in water. PEO is available on the basis of molecular weight. Both PEO and HPMC are useful alone. Alternatively, mixtures of the two materials, or mixtures of various viscosities or molecular weights of either compound may be used in the present invention. Carbopol 934P (carboxypolymethylene) may also be added.

It was found that it is the concentration of polymer (hydrophilic moiety) and dicalcium phosphate (hydrophobic ingredient) which is responsible for the desired release of the drug from the tablet. At high DCP concentration (above 90%), hydrophobicity of DCP played a major role in initial slowing of the release and the release essentially followed due to erosion. While at low DCP concentration or high polymer concentration polymer swelling played a major role in the release. Hence it is the concentration of polymer and other excepients which affects the release of the drug from the dosage forms.

Evaluation Parameters

Assay

The assay was carried out as described in British Pharmacopoiea for Glipizide Tablets. The content was found to be between 95% to 105% of the stated amount (27).

Content Uniformity

The test substance complied with the content uniformity determination(28).

Weight Variation

Twenty units were taken at random and the average weight was determined. Not more than two of the individual weights deviated from the average weight more than 7.55 (for a tablet more than 80 mg and less than 250 mg) (29).

Drug Release and Dissolution Studies

Dissolution testing has been recognized as a relatively fast and inexpensive in vitro technique that can be utilized in the assessment of the release characteristics of dosage forms under investigation. Over the past 10–15 years it has been established that dissolution testing is probably the most important in vitro test that can be used to assess and control variables associated with formulation excipients, design and manufacturing, which may alter the release characteristics of the active moiety from the formulation. Currently dissolution testing is therefore implemented in the assessment in the evaluation of the release rates and bioavailability of dosage forms. Recognition of the importance of dissolution testing has resulted in dissolution testing requirements being incorporating into official (30) compendia such as United States Pharmacopeia.

Drug absorption from a solid dosage form after oral administration depends on the release of the drug substance from the drug product, the dissolution or solubilization of the drug under physiological conditions, and the permeability across the gastrointestinal tract. Because of the critical nature of the first two of these steps, in vitro dissolution may be relevant to the prediction of in vivo performance.

Based on this general consideration, in vitro dissolution tests for dosage forms are used to (1) assess the lot to lot quality of a drug product, (2) guide development of new formulations; and (3) ensure continuing product quality and performance after certain changes, in the formulation, the manufacturing process, the site of manufacture, and the scale-up of the manufacturing process.

Based on drug solubility and permeability, the following Biopharmaceutics classification system (BCS) is recommended in the literature (31)

| | |
|---|---|
| Case 1: | High solubility - High permeability drugs |
| Case 2: | Low solubility - High permeability drugs |
| Case 3: | High solubility - low permeability drugs |
| Case 4: | High solubility - low permeability drugs |

This classification can be used as a basis for setting in vitro dissolution specifications and can also provide a basis for predicting the likelihood of achieving a successful in vitro-in vivo correlation (IVIVC). The solubility of a drug is determined by dissolving the highest unit dose of the drug in 250 ml of buffer adjusted between pH 1.0 to 8.0. In the case of low solubility/high permeability drugs (case 2), drug dissolution may be the rate limiting step for drug absorption and an IVIVC may be expected (32). A dissolution profile in multiple media is recommended for drug products in this category.

Dissolution Specifications

In vitro dissolution specifications should generally be based on the performance of the clinical/bioavailability lots. These specifications may sometimes be widened so that scale up lots, as well as stability lots, meet the specifications associated with the clinical/bioavailability lots. This approach is based on the use of the drug is the dissolution test as a quality control test without any in vivo significance, even though in certain cases (e.g., ER formulations), the rate limiting step in the absorption of the drug is the dissolution of the drug from the formulation. An IVIVC adds in vivo relevance to in vitro dissolution specifications, beyond batch to batch quality control. In this approach, the in vitro dissolution test becomes a meaningful predictor of in vivo performance of the formulation.

Setting Dissolution Specifications without an IVIVC: USP acceptance criteria for dissolution testing are recommended unless alternate acceptance criteria are specified. Hence, studies of controlled release dosage forms of glipizide were carried out using 6 dosage units of the test drug. The protocols and procedures as described in the guidelines to drug testing by FDA (33,34), were used.

| | |
|---|---|
| Apparatus: | USP XXIII apparatus I (Pharmatest model PTW II) |
| RPM | 75 rpm |
| Medium | Simulated Intestinal Fluid (SIF) (without enzyme) pH 7.5. The medium was 6.804 gm of potassium dihydrogen orthophosphate/1000 ml distilled water adjusted to pH 7.5 by NaOH. |
| Volume | 900 ml |
| Sampling Times | 1 hr, 2 hr, 3 hr, 4 hr, 5 hr, 6 hr, 8 hr, 10 hr, 12 hr, 18 hr and 24 hr |
| Analytical | Validated method (35) |

Dissolution Profile Comparisons

Dissolution profiles may be considered similar by virtue of (1) overall profile similarity, and (2) similarity at every dissolution sample time point. The dissolution profile comparison may be carried out using model independent or model dependent methods (36–38).

Model Independent Approach Using a Similarity Factor

A simple model independent approach uses a difference factor ($f_1$) and a similarity factor ($f_2$) to compare dissolution profiles. The difference factor ($f_1$) calculates the percent (%) difference between the two curves at each time point and is a measurement of the relative error between the two curves:

$$f_1 = \left\{ \left[ \sum_{t=1}^{n} |R_t - T_t| \right] / \left[ \sum_{t=1}^{n} R_t \right] \right\} 100$$

where n is the number of time points, $R_t$ is the dissolution value of the reference batch at time t, and $T_t$ is the dissolution value of the test batch at time t.

The similarity factor ($f_2$) is a logarithmic reciprocal square root transformation of the sum of squared error and is a measurement of the similarity in the percent (%) dissolution between the two curves.

$$f_2 = 50 \log \left\{ \left[ 1 + (1/n) \sum_{t=1}^{n} (R_t - T_t)^2 \right]^{-0.5} \times 100 \right\}$$

$f_2$ values greater than 50 (50–100) ensure sameness or equivalence of the two curves and, thus, of the performance of the test and reference products.

A specific procedure to determine difference and similarity factors is as follows:

1. Determine the dissolution profile of two products (12 units each) of the test and reference products.
2. Using the mean dissolution values from both curves at each time interval, calculate the difference factor ($f_1$) and similarity factor ($f_2$) using the above equations.
3. For curves to be considered similar, $f_1$ values should be close to 0, and $f_2$ values should be close to 100. Generally, $f_1$ values up to 15 (0–15) and $f_2$ values greater than 50 (50–100) ensure sameness or equivalence of the two curves and, thus, of the performance of the test and reference products.

This model independent method is most suitable for dissolution profile comparison when three to four or more dissolution time points are available. As further suggestions for the general approach, the following recommendations should also be considered:

The dissolution measurements of the test and reference batches should be made under exactly the same conditions. The dissolution time points for both the profiles should be the same (e.g., 15, 30, 45, 60 minutes). The reference batch used should be the most recently manufactured prechange product.

Only one measurement should be considered after 85% dissolution of both the products.

To allow use of mean data, the percent coefficient of variation at the earlier time points (e.g., 15 minutes) should not be more than 20%, and at other time points should not be more than 10%.

Methods to Document BA (Bioavailabiltiy) and be (Bioequivalence)

Bioavailability

The rate and extent to which an active ingredient or active moiety is absorbed from a drug product and becomes available to the site of action.

Bioequivalence

It is defined as the absence of a significant difference in the rate and extent to which the active ingredient or active moiety in pharmaceutical equivalents or pharmaceutical alternatives becomes available at the site of drug action when administered at the same molar dose under similar conditions in an appropriately designed study.

As noted at 21 CFR 320.24, several in vivo and in vitro methods can be used to measure product quality BA and establish BE. In descending order of preference, these include pharmacokinetic, pharmacodynamic, clinical, and in vitro studies (39).

A. Pharmacokinetic Studies

General Considerations The statutory definitions of BA and BE, expressed in terms of rate and extent of absorption of the active ingredient or moiety to the site of action, emphasize the use of pharmacokinetic measures in an accessible biological matrix such as blood, plasma, and/or serum to indicate release of the drug substance from the drug product into the systemic circulation. This approach rests on an understanding that measuring the active moiety or ingredient at the site of action is generally not possible and, furthermore, that some relationship exists between the efficacy/safety and concentration of active moiety and/or its important metabolite or metabolites in the systemic circulation.

B. Pharmacodynamic Studies

Pharmacodynamic studies are not recommended for orally administered drug products when the drug is absorbed into the systemic circulation and a pharmacokinetic approach can be used to assess systemic exposure and establish BE. However, in those instances where a pharmacokinetic approach is not possible, suitably validated pharmacodynamic methods can be used to demonstrate BE.

C. Comparative Clinical Studies

Where there are no other means, well-controlled clinical trials in humans may be useful to provide supportive evidence of BA or BE. However, the use of comparative clinical trials as an approach to demonstrate BE is generally considered insensitive and should be avoided where possible (21 CFR 320.24). The use of BE studies with clinical trial endpoints may be appropriate to demonstrate BE for orally administered drug products when measurement of the active ingredients or active moieties in an accessible biological fluid (pharmacokinetic approach) or pharmacodynamic approach is infeasible.

D. In vitro Studies

Under certain circumstances, product quality BA and BE can be documented using in vitro approaches (21 CFR 320.24). For highly soluble, highly permeable, rapidly dissolving, orally administered drug products, documentation of BE using an in vitro approach (dissolution studies) is appropriate based on the biopharmaceutics classification system. This approach may also be suitable under some circumstances in assessing BE during the IND period, for NDA and ANDA submissions, and in the presence of certain postapproval changes to approved NDAs and ANDAs. In addition, in vitro approaches to document BE for nonbioproblem drugs approved prior to 1962 remain acceptable (21 CFR 320.33). Dissolution testing is also used to assess batch-to-batch quality, where the approach may become one of the tests, with defined procedures, in a drug product specification to allow batch release. Dissolution testing is also used to (1) provide process control and quality assurance, and (2) assess the need for further BE studies relative to minor postapproval changes, where dissolution can function as a signal of bioinequivalence. in vitro dissolution characterization is encouraged for all product formulations investigated (including prototype formulations), particularly if in vivo absorption characteristics are being defined for the different product formulations. Such efforts may enable the establishment of an in vitro-in vivo correlation. When an in vitro-in vivo correlation or association is available (21 CFR 320.22), the in vitro test can serve not only as a quality control specification for the manufacturing process, but also as an indicator of how the product will perform in vivo.

Mucoadhesion Studies

There is a need to provide oral GI formulations that are safe, efficacious and have sufficient dwell or contact time with the GI mucosa. Such formulations should have excellent mucosal coating properties for both the upper and lower GI tract, i.e., they should have mucoadhesive or bioadhesive properties. Since the slightly water-soluble drugs do not by themselves possess such bioadhesive or mucoadhesive properties, the formulations containing them must provide the same. Hence the polymer used in the formulation has mucoadhesive properties and can increase the residence time of the formulation in the GIT (gastrointestinal tract). Polyethylene oxide has got proven mucoadhesion (40–44).

Mucoadhesion studies were carried out by the modification of the method reported in the literature (45). The technique utilized the concept of a double beam physical balance. Washed and cleaned mucosa from the pig stomach was used as biological membrane and force of detachment was calculated for all the formulations. Force of detachment is the force required to pull apart the tablet from the testing mucosa and it was calculated using formula: Force of detachment=Actual weight for detachment×g where, g is the acceleration due to gravity (980 cm/sec$^2$), and $$\text{Force of detachment per unit area (dynes/cm}^2\text{)} = \frac{\text{Force of detachment (dynes)}}{\pi \times r^2}$$

where r is the radius of the tablet in cm

Mucoadhesion of the formulations was found to increase with increase in polymer concentration and increase in polymer weight. Hence at high polymer concentration, one can expect the residence time of the formulation can increase and the release can be modified using cyclodextrins or other excepients which make the release fast. The results are shown in Table 3.

Stability Studies at Standard Storage Conditions

The drug as well as the excepients were stable, nonhygroscopic, non degradable when evaluated repeatedly after 3 months during 12 months protocol (46).

Mechanism of Release of Drug from the Matrix

During the release of drugs from hydrophilic matrices of PEO or HPMC, two mechanistic phenomena take place: the swelling and the erosion of the polymer. The release kinetics of the drug from the tablet are dependent upon the relative magnitude of the rate of polymer swelling at the moving rubbery/glassy front and the rate of polymer erosion at the swollen polymer/dissolution medium front. It is most preferable to attain the synchronization of the velocities of the swelling front and the erosion front in order to achieve zero-order release kinetics from hydrophilic polymer matrices.

Ritger and Peppas (47) introduced a simple exponential relation to describe the general solute release behavior of controlled release polymeric devices. It was shown that this equation can adequately describes the release of drugs regardless of the release mechanism. The expression can be given by $$\frac{M_t}{M_\alpha} = kt^n \qquad \text{Equation 1}$$

where $$\frac{M_t}{M_\alpha}$$

is the fractional solute release, t is the time, k is kinetic constant and n is the diffusion exponent. In swelling controlled systems, the dissolution medium surrounding the controlled release device may enter the polymer at a rate that controls the drug release. The prevailing molecular mechanism is a coupling of diffusion and macromolecular relaxation as a result of which the drug diffuses outward with a kinetic behavior that is dependent upon the relative ratio of diffusion and relaxation.

$$\frac{M_t}{M_\alpha} = k_1 \sqrt{t} + k_2 t \qquad \text{Equation 2}$$

where $k_1$ is fickion contribution constant and $k_2$ is the relaxation contribution constant.

Drug release from hydrophilic polymer tablets is governed by swelling/drug diffusion or swelling/polymer erosion depending upon the characteristics of the different molecular weights of the hydrophilic polymers and their concentration in the matrix.

Conversely, the delivery of an insoluble pharmaceutical agent is dictated only by the erosion of the swollen polymer layer, since there will be no diffusion and dissolution of the pharmaceutical agent out of the swollen polymer matrix. Accordingly, relatively slow swelling and eroding polymers can be used. In this case, if a sufficiently slow polymer is used, a tablet can be made very small with a higher concentration of pharmaceutical agent than would be used in a normal-sized tablet. This would result in a very small but very effective sustained release tablet.

Referring also to FIG. 1 through FIG. 4, examples provided here show that formulations of the invention may comprise different amounts and ratios of active ingredient and excipient material. Further, different excipients can be used. Particularly preferred excipients and amounts used are recited in the Examples. However, upon reading the disclosure those skilled in the art will come to understand the general concepts of the invention and will recognize that other excipients, amounts, ratios and combinations might be used to obtain the desired results.

Test Formulations

All the formulations prepared by using the polymer given in the examples.

Reference Formulations

Glucotrol XL 5 mg, 10 mg, 20 mg (Pfizer Inc. USA) and Glytop 5SR (Sidmak Laboratories Ltd. India)

Figure 4:
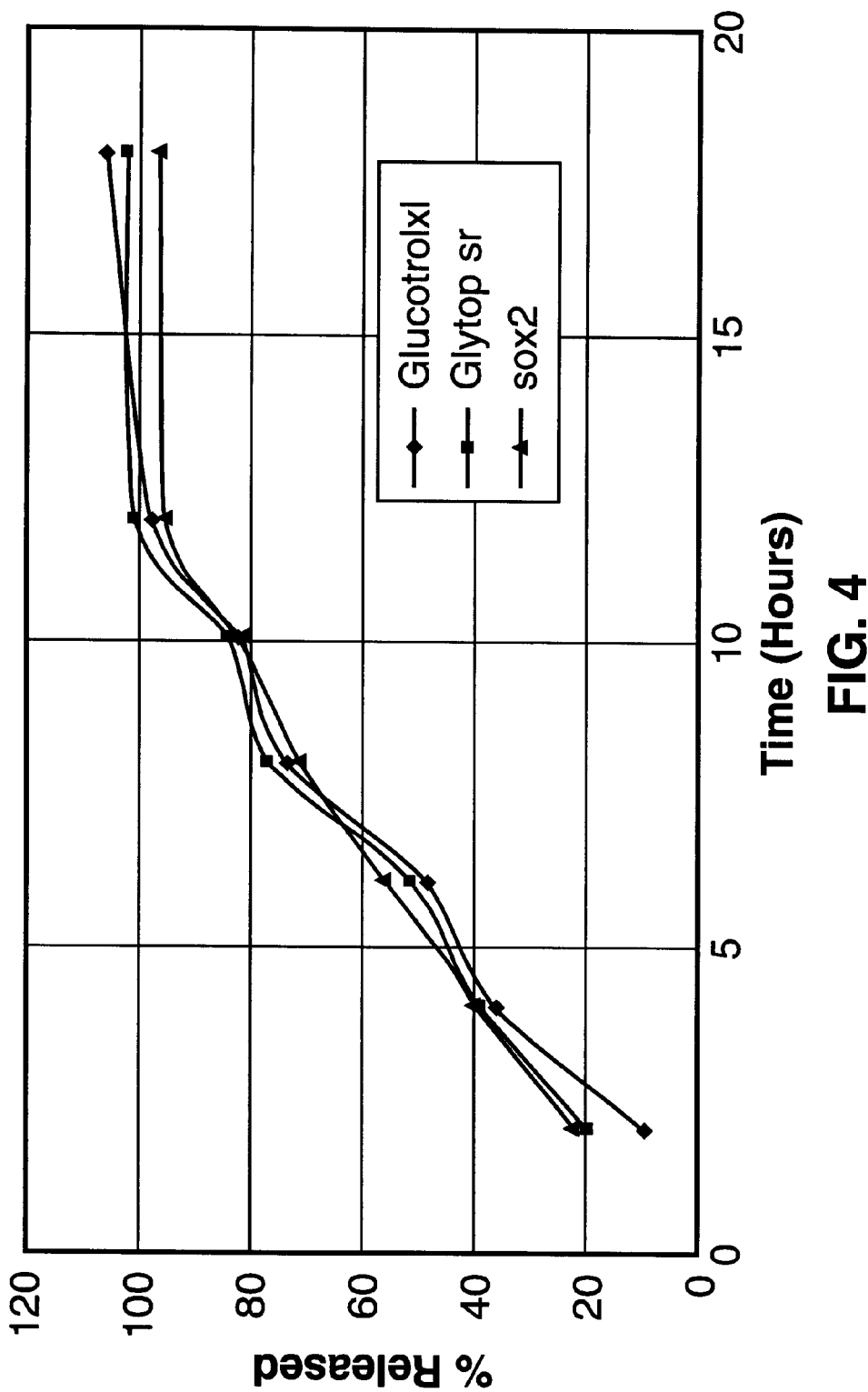
FIG. 4 is a graph comparing polyethylene oxide formulations with glucotrolxl (Pfizer, USA) and glytop SR (Sidmark Lab, India).

The selected formulation has been coded as SOX 2 in FIG. 4.

In vitro Test to Carry Out Bioequivalence

Dissolution testing can be used to determine the bioequivalence of a test product with the reference product by comparing the dissolution profiles of the test product with the reference product.

The invention is further explained with the help of following examples, which should not be construed to limit the scope of the invention.

EXAMPLES

| (1) | Polyethylene Oxide (Molecular wt. 4000,000) | 15% |
| | Drug | 5% |
| | Magnesium Stearate | 1% |
| | Dicalcium Phosphate | q.s. |
| (2) | Polyethylene Oxide (Molecular wt. 4000,000) | 20% |
| | Drug | 5% |
| | Magnesium Stearate | 1% |
| | Dicalcium Phosphate | q.s. |
| (3) | Polyethylene Oxide (Molecular wt. 4000,000) | 25% |
| | Drug | 5% |
| | Magnesium Stearate | 1% |
| | Dicalcium Phosphate | q.s. |
| (4) | Polyethylene Oxide (Molecular wt. 4000,000) | 30% |
| | Drug | 5% |
| | Magnesium Stearate | 1% |
| | Dicalcium Phosphate | q.s. |
| (5) | Polyethylene Oxide (Molecular wt. 4000,000) | 40% |
| | Drug | 5% |
| | Magnesium Stearate | 1% |
| | Talc | 1% |
| | Dicalcium Phosphate | q.s. |
| (6) | Polyethylene Oxide (Molecular wt. 4000,000) | 60% |
| | Drug | 5% |
| | Magnesium Stearate | 1% |
| | Dicalcium Phosphate | q.s. |
| (7) | Polyethylene Oxide (Molecular wt. 4000,000) | 94% |
| | Drug | 5% |
| | Magnesium Stearate | 1% |
| | Dicalcium Phosphate | q.s. |

-continued

| (8) | Polyethylene Oxide (Molecular wt. 4000,000) | 93% |
| | Drug | 5% |
| | Magnesium Stearate | 1% |
| | βcyclodextrin | 1% |
| | Dicalcium Phosphate | q.s. |
| (9) | Polyethylene Oxide (Molecular wt. 7000,000) | 10% |
| | Drug | 5% |
| | Magnesium Stearate | 1% |
| | βcyclodextrin | 1% |
| | Dicalcium Phosphate | q.s. |
| (10) | Polyethylene Oxide (Molecular wt. 7000,000) | 20% |
| | Drug | 5% |
| | Magnesium Stearate | 1% |
| | Dicalcium Phosphate | q.s. |
| (11) | Polyethylene Oxide (7000,000) | 40% |
| | Drug | 5% |
| | Magnesium Stearate | 1% |
| | Talc | 1% |
| | Dicalcium Phosphate | quantity sufficient |
| (12) | Polyethylene Oxide (Molecular wt. 7000,000) | 60% |
| | Drug | 5% |
| | Magnesium Stearate | 1% |
| | Dicalcium Phosphate | q.s. |
| (13) | Polyethylene Oxide (Molecular wt. 4000,000) | 20% |
| | Drug | 10% |
| | Magnesium Stearate | 1% |
| | Dicalcium Phosphate | q.s. |
| (14) | Polyethylene Oxide (Molecular wt. 4000,000) | 40% |
| | Drug | 10% |
| | Magnesium Stearate | 1% |
| | Dicalcium Phosphate | q.s. |
| (15) | Polyethylene Oxide (Molecular wt. 4000,000) | 60% |
| | Drug | 10% |
| | Magnesium Stearate | 1% |
| | Dicalcium Phosphate | q.s. |
| (16) | Polyethylene Oxide (Molecular wt. 4000,000) | 89% |
| | Drug | 10% |
| | Magnesium Stearate | 1% |
| | Dicalcium Phosphate | q.s. |
| (17) | Polyethylene Oxide (Molecular wt. 7000,000) | 20% |
| | Drug | 10% |
| | Magnesium Stearate | 1% |
| | Dicalcium Phosphate | q.s. |
| (18) | Polyethylene Oxide (Molecular wt. 7000,000) | 40% |
| | Drug | 10% |
| | Magnesium Stearate | 1% |
| | Dicalcium Phosphate | q.s. |
| (19) | Polyethylene Oxide (Molecular wt. 7000,000) | 15% |
| | Drug | 5% |
| | Magnesium Stearate | 1% |
| | Dicalcium Phosphate | q.s. |
| (20) | Polyethylene Oxide (Molecular wt. 7000,000) | 25% |
| | Drug | 5% |
| | Magnesium Stearate | 1% |
| | Dicalcium Phosphate | q.s. |
| (21) | Polyethylene Oxide (Molecular wt. 4000,000) | 20% |
| | Drug | 10% |
| | Magnesium Stearate | 1% |
| | Lactose | q.s. |
| (22) | Polyethylene Oxide (Molecular wt. 4000,000) | 60% |
| | Drug | 10% |
| | Magnesium Stearate | 1% |
| | Lactose | q.s. |
| (23) | Polyethylene Oxide (Molecular wt. 7000,000) | 20% |
| | Drug | 10% |
| | Magnesium Stearate | 1% |
| | Lactose | q.s. |
| (24) | Polyethylene Oxide (Molecular wt. 4000,000) | 40% |
| | Drug | 10% |
| | Magnesium Stearate | 1% |
| | Lactose | q.s. |
| (25) | Polyethylene Oxide (Molecular wt. 7000,000) | 60% |
| | Drug | 10% |
| | Magnesium Stearate | 1% |
| | Dicalcium Phosphate | q.s. |
| (26) | Polyethylene Oxide (Molecular wt. 4000,000) | 60% |
| | Drug | 10% |
| | Magnesium Stearate | 1% |
| | Lactose | q.s. |

-continued

| | | |
|---|---|---|
| (27) | Polyethylene Oxide (Molecular wt. 4000,000) | 84% |
| | Drug | 10% |
| | Magnesium Stearate | 1% |
| | βcyclodextrin | 5% |
| | Lactose | q.s. |
| (28) | Hydroxypropylmethyl cellulose (K15M) | 20% |
| | Drug | 5% |
| | Magnesium Stearate | 1–3% |
| | Talc | 1–3% |
| | Dicalcium Phosphate | q.s. |
| (29) | Hydroxypropylmethyl cellulose (K15M) | 20% |
| | Drug | 5% |
| | Magnesium Stearate | 1–3% |
| | PEG 6000 | 20% |
| | Dicalcium Phosphate | q.s. |
| (30) | Hydroxypropylmethyl cellulose (K4M) | 25% |
| | Drug | 5% |
| | Magnesium Stearate | 1–3% |
| | Carbopol 934 P | 25% |
| | Dicalcium Phosphate | q.s. |
| (31) | Hydroxypropylmethyl cellulose (K4M) | 5% |
| | Drug | 5% |
| | Magnesium Stearate | 1–3% |
| | Carbopol 934 P | 10% |
| | Dicalcium Phosphate | q.s. |
| (32) | Hydroxypropylmethyl cellulose (K15M) | 10% |
| | Drug | 5% |
| | Magnesium Stearate | 1–3% |
| | Carbopol 934 P | 5% |
| | Dicalcium Phosphate | q.s. |
| (33) | Hydroxypropylmethyl cellulose (K15M) | 25% |
| | Drug | 5% |
| | Magnesium Stearate | 1–3% |
| | Carbopol 934 P | 20% |
| | Beta Cyclodextrin | 10% |
| | Dicalcium Phosphate | q.s. |
| (34) | Polyethylene Oxide (Molecular wt. 4000,000) | 20% |
| | Drug | 20% |
| | Magnesium Stearate | 1% |
| | βcyclodextrin | 15% |
| | Lactose | q.s. |
| (35) | Polyethylene Oxide (Molecular wt. 4000,000) | 30% |
| | Drug | 20% |
| | Magnesium Stearate | 1% |
| | βcyclodextrin | 20% |
| | Lactose | q.s. |
| (36) | Polyethylene Oxide (Molecular wt. 4000,000) | 40% |
| | Drug | 20% |
| | Magnesium Stearate | 1% |
| | βcyclodextrin | 20% |
| | Lactose | q.s. |

Tablets of different thickness, weight and diameters were prepared and the release kinetics were observed.

The ingredients (PEO, HPMC, Carbopol, drug, magnesium stearate, and other additives) were homogeneously mixed and then tableted using a single punch tablet machine. A set of tablet punches with flat surfaces were used to prepare tablets of various diameters, including 7 mm, 8 mm, 9 mm, and 11 mm. The hardness of the resulting tablets was 5 Kg. The weight of the tablets was dependent upon the dose of glipizide.

In vitro release of drugs from the different formulation tablets was carried out by using the USP basket procedure in simulated intestinal fluid (without pancreatin) at a stirring rate of 75 rpm and 37° C. as recommended by FDA. The amount of drug released was analyzed by HPLC using buffer:acetonitrile (50:50) as mobile phase with flow rate 1.5 ml/min using $C_{18}$, Phenomenax, 30 cm column. The release kinetic data (up to 60% release) were treated by equation (1) above. Dissolution profiles of the formulations (test products) were compared with the reference products (Glucotrol XL of Pfizer and Glytop SR of Sidmak Lab)

As shown in Table 1 Change in the diluent from lactose to DCP resulted in the release from zero-order to non fickian type. DCP added to the retardation property of the polymer due to hydrophobic property of the Dicalcium Phosphate. Lactose (a water soluble excepient) mixed with the polymer matrix reduces the polymer content and enhances the hydration of the polymer through osmotic pressure. As shown in FIG. 1, the addition of lactose did not significantly affect the release kinetics other than to shorten the period of release. A reduction in the concentration of lactose with a simultaneous increase in the content of the poymer, resulted in a reduction in release rate. In the case of DCP formulations, when the polymer concentration was increased from 5% to 20%, it led to retardation of the release, however at 25% concentration, the hydrophilicity of the polymer dominated as compared to the hydrophobcity of DCP and release enhanced. On further increasing the polymer concentration, the release retarded because of the thickness of gel layer increased with increase in polymer concentration.

At lower polymer concentration, zero order release (values of n approaching 1) was obtained because rate of swelling of gel layer was equal to the rate of dissolution or erosion of the polymer while at high concentration of polymers nonfickian release (0.4<n<1) was obtained.

A relatively high value of $k_1$ and a decreased value of $k_2$ for formulations made with DCP as a diluent indicate the predominance of fickian diffusion mechanism. In case of lactose formulations, the fickian fraction of the drug released becomes higher and release occurs by the polymer relaxation.

The diffusion of water into the polymer matrix is not greatly facilitated by the water uptake of drugs but rather by the water uptake of the hydrophilic polymer. This demonstrates that the swelling/erosion of the polymer is the controlling variable rather than the diffusion of drugs through the swollen gel layer.

PEO tablets were also tested to determine the effect of stirring on the release of a drug from the tablet. The rate of release of the drug from the PEO tablet increased as stirring was increased with an increase in the stirring rate from 100 to 200 rpm. However, below 100 rpm, the rate of release of the drug was insensitive to the amount of stirring. The insensitivity of PEO tablets to the stirring rate also makes PEO a good candidate for oral dosage forms since the release rate will not vary as the tablet is subjected to turbulence in the stomach and intestine.

For systems controlled by the erosion of polymer followed by dissolution of the drug from the polymer, it may be necessary to vary the size of the tablet to achieve the desired release kinetics.

The suspended drug acts as a reservoir and the release rate of the drug from the PEO tablets is balanced with the dissolution rate of the suspended drug resulting in constant release kinetics. In contrast, for extended release dosage forms of highly water soluble drugs, the drug release is coincidental with the disappearance of the swollen polymer. That is, as the swollen polymer is dissolved, the drug is simultaneously released and dissolved in the dissolution medium. If the dissolution medium does not solubilize the released drug during this period, the excess amount of the drug will become suspended and precipitate. Incorporating a solubilizing agent into the PEO tablets will aid in releasing low solubility drugs from the tablets. As the period of release increases the amount of the suspended drug will decrease causing the release profile to gradually tail off towards complete release. Hence the release kinetics can be improved by the addition of βcyclodextrins.

Figure 2:
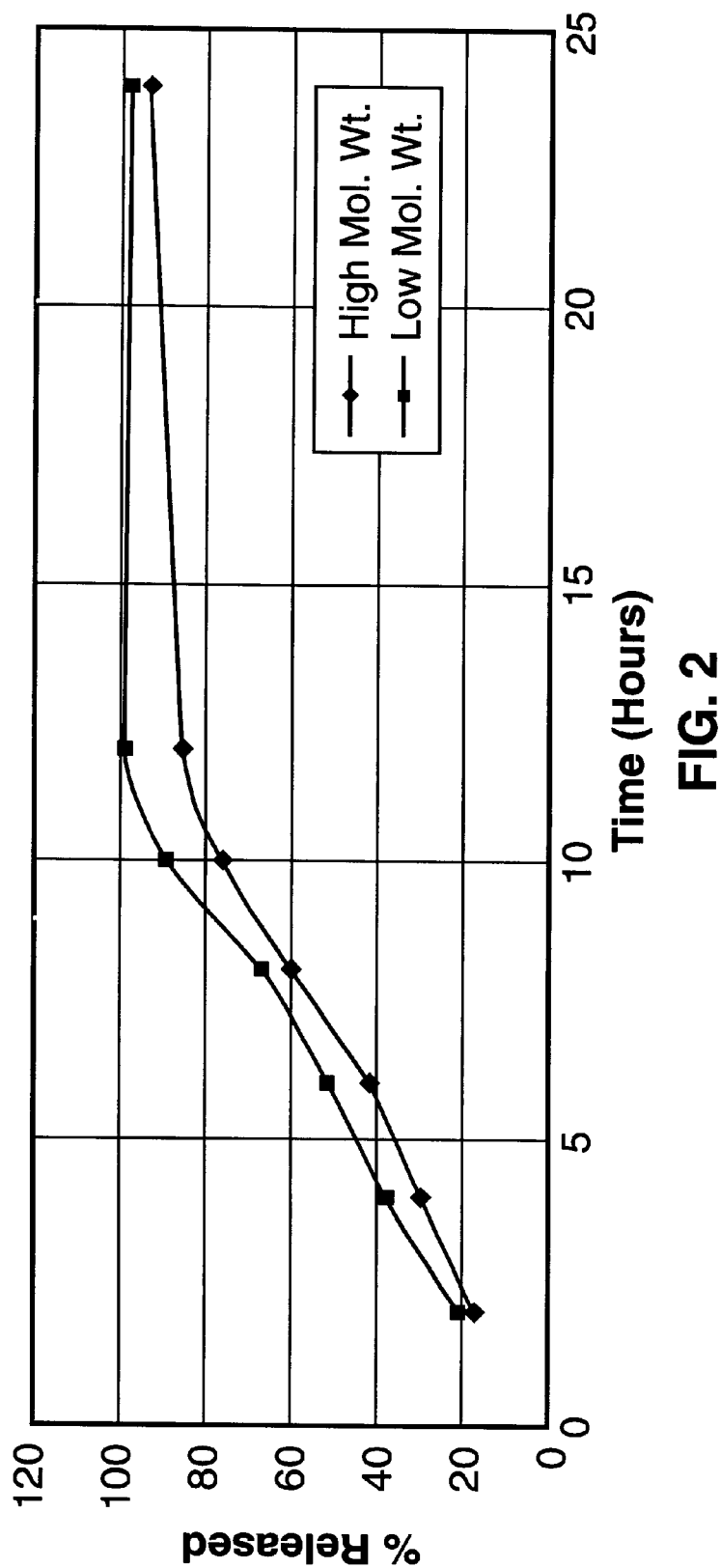
FIG. 2 is a graph showing the effect of PEO molecular weight on the release of glipizide.
Figure 3:
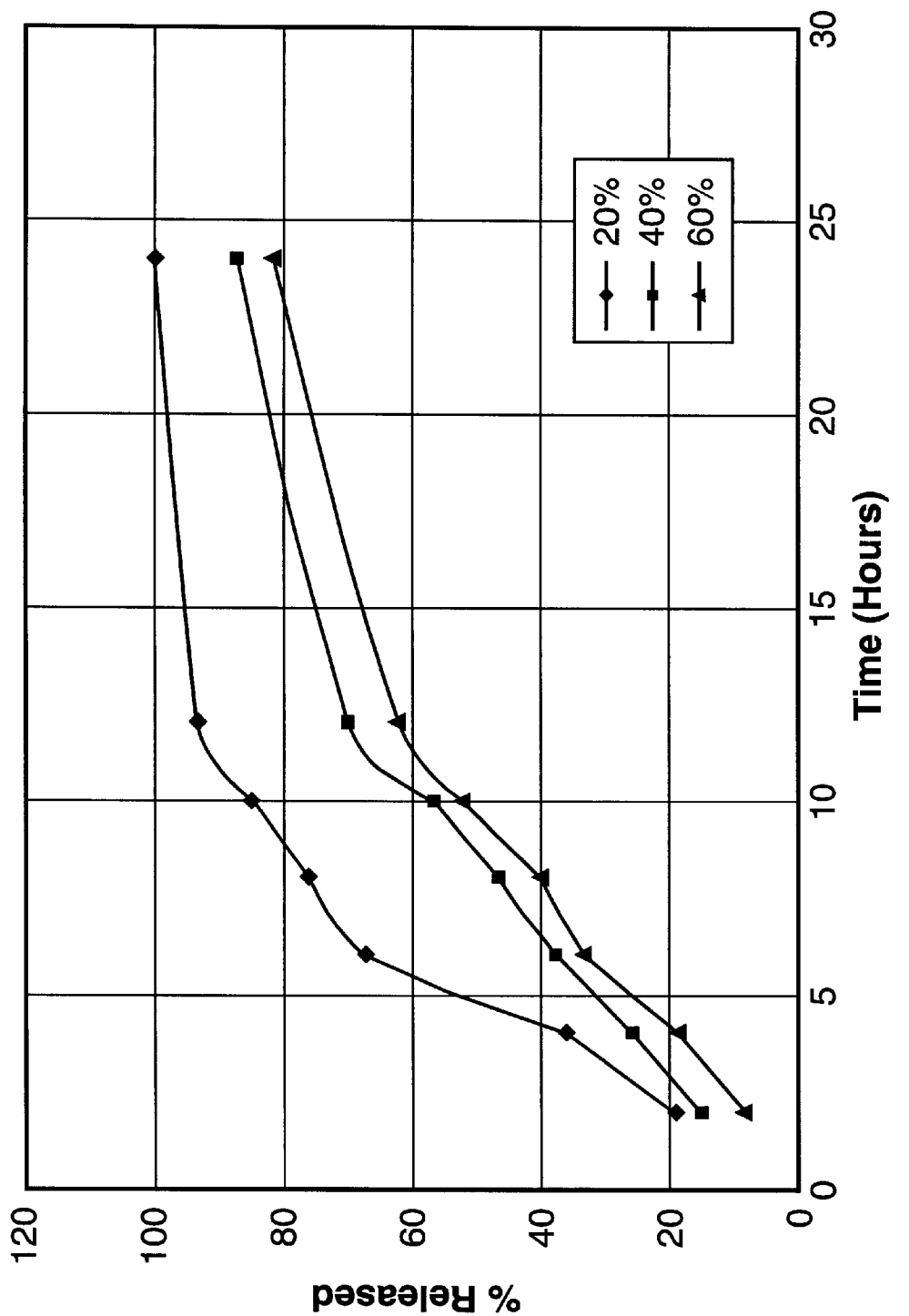
FIG. 3 is a graph showing the effect of polymer concentration on the release of glipizide.

FIGS. 2 and 3 show the effect of PEO molecular weight and concentration of polymer on release of glipizide from tablets The rate of dissolution (erosion) of hydrophilic polymers decreases with increasing molecular weight. This causes different molecular weights of PEO to have different values for the release exponent (n). The synchronization of the gel layer thickness takes place earlier with the low molecular weight PEO and shortly after the outer diameter starts becoming smaller. The higher the molecular weight, the later the synchronization takes place. However, for a higher molecular weight PEO tablet and at very high concentration of the polymers the synchronization of the gel layer did not occur and the gel layer thickness increased until the entire tablet was in gel form. After the front meets at the core of the tablet, the swollen gel lasts a much longer time than other swellable/erodible polymers. As a result of this long residence time of the gel layer, it is expected that the release kinetics are governed by the erosion/drug diffusion process after the swelling front meets at the core of the tablet.

Accordingly, the synchronized gel thickness plays an important role on the release kinetics at the early time of drug release. As the molecular weight of the polymer increases, the dissolution rate of the polymer decreases compared to the swelling rate of the polymer. The "dissolution rate" and the "erosion rate" are used here interchangeably. In actuality, the decrease in the size of the swollen gel layer is due both to erosion and dissolution. Due to the low dissolution rate, the thickness of the polymer layer increases. Drug diffusion through the swollen gel layer then becomes the foremost process controlling the release mechanism. With high molecular weight (or high viscosity grade) polymers of PEO and HPMC, the swelling of the polymer is the dominant step in controlling release kinetics over the erosion of swollen polymer. With low molecular weight polymers of PEO and HPMC, the erosion of the polymer is the rate determining step for the release kinetics. However, the degree of swelling of PEO is higher than HPMC resulting in more favorable kinetics for PEO than for HPMC.

FIG. 4 shows the release profiles of Glucotrol XL(5 mg), Glytop SR (5 mg) and PEO formulation (with highest $f_2$ value). Table 2 shows the $T_{50}$, $T_{60}$, $T_{70}$, $T_{80}$ and $T_{90}$ values for all the examples and marketed formulations. Release profiles of the formulations can be compared by $f_2$ values. All the formulations having $f_2$ values 50–100 are considered to be bioequivalent.

All the formulations were analyzed on the basis of Model Independent approach using similarity factor ($f_2$). A value of $f_2$ between 50–100 ensures equivalence of two dissolution curves. Therefore, all the formulations with $f_2$ values 50–100 (as shown in table 1) can be considered equivalent to the marketed one. Formulations with maximum $f_2$ values will be considered best for phase I clinical trials.

Range to obtain the desired formulation with particular amount of drug

| | | |
|---|---|---|
| (1) | Polyethylene Oxide (Molecular wt. 4000,000) | 15–40% |
| | Drug (Glipizide or other water insoluble drug | 5% |
| | Magnesium Stearate | 1% |
| | Dicalcium Phosphate | q.s. |
| (2) | Polyethylene Oxide (Molecular wt. 7000,000) | 10–40% |
| | Drug | 5% |
| | Magnesium Stearate | 1% |
| | Dicalcium Phosphate | q.s. |

-continued

| | | |
|---|---|---|
| (3) | Polyethylene Oxide (Molecular wt. 4000,000) | 20–40% |
| | Drug | 10% |
| | Magnesium Stearate | 1% |
| | Dicalcium Phosphate | q.s. |
| (4) | Polyethylene Oxide (Molecular wt. 7000,000) | 20–40% |
| | Drug | 10% |
| | Magnesium Stearate | 1% |
| | Lactose | q.s. |

Ranges with which the desired results could not be achieved

| | | |
|---|---|---|
| (1) | Polyethylene Oxide (Molecular wt. 4000,000) | 60–90% |
| | Glipizide and other low dosed water insoluble drug | 5% |
| | Magnesium Stearate | 1% |
| | Lactose | q.s. |
| (2) | Polyethylene Oxide (Molecular wt. 4000,000) | 2–12% |
| | Glipizide and other low dosed water insoluble drug | 5% |
| | Magnesium Stearate | 1% |
| | Lactose | q.s. |
| (3) | Polyethylene Oxide (Molecular wt. 4000,000) | 45–80% |
| | Glipizide and other low dosed water insoluble drug | 10% |
| | Magnesium Stearate | 1% |
| | Lactose | q.s. |

Advantages of the invention over already available osmotic pump (pfizer) formulation 1) A warning is given while giving osmotic pump formulations, "As with any other non-deformable material, caution should be used when administering glipizide extended release (osmotic pump) tablets in patients with preexisting severe gastrointestinal narrowing (pathologic or iatrogenic)" while this invention can be used for such patients too as the tablet is dissolved completely by the time the drug is released.
2) Glucotrol XL consists of a bilayer tablet core that contains drug in the upper compartment and an osmotic polymeric driving agent in the lower push compartment. The core system is coated with semipermeable membrane with a release orifice formed after the coating operation. The rate of solute delivery by the system is constant as long as excess solid is present in the device, but the rate declines periodically towards zero once the concentration falls below saturation. Preparation of this osmotic pump is very complicated as compared to this invention. Our formulation simply requires mixing and direct compression of the excepients.
3) As an osmotic pump must contain an excess amount of drug to maintain a saturated concentration and constant release hence an extra amount of drug (more than the dose) is added. This makes the formulation costly as compared to the above mentioned invention.
4) Since polyethylene oxide has got proven mucoadhesion due to which the residence time of the tablet in g.i.t. may increase leading to effective levels of the drug for more than 24 hours
5) Above mentioned formulation can include any of the low dosed (30–40 mg) water insoluble drug.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Evaluation parameters of different formulations

| Example No. | k | n | $k_1$ | $k_2$ | $f_2$ (compared to glucotrol XL, Pfizer) | $f_2$ (compared to Glytop SR, Sidmak lab) |
|---|---|---|---|---|---|---|
| 1 | 0.1219 | 0.8885 | 1.0311 | 0.0900 | 62.47 | 70.88 |
| 2 | 0.1241 | 0.9429 | 0.9944 | 0.0977 | 50.01 | 52.48 |
| 3 | 0.2852 | 0.4997 | 1.3317 | −0.0035 | 41.96 | 50.37 |
| 4 | 0.2647 | 0.4848 | 1.3038 | 0.0026 | 43.82 | 52.3058 |
| 5 | 0.0971 | 0.7491 | 1.0609 | 0.0415 | 32.24 | 31.027 |
| 6 | 0.0562 | 0.8563 | 1.0089 | 0.0469 | 23.24 | 22.62 |
| 7 | 0.0933 | 0.7071 | 1.0598 | 0.0416 | 22.63 | 21.78 |
| 8 | 0.0804 | 0.7241 | 1.0406 | 0.0441 | 29.15 | 27.20 |
| 9 | 0.2442 | 0.4387 | 1.2709 | −0.0029 | 44.94 | 48.79 |
| 10 | 0.2879 | 0.4584 | 1.3662 | −0.0083 | 38.43 | 44.72 |
| 11 | 0.2310 | 0.4772 | 1.224 | 0.0048 | 43.63 | 46.20 |
| 12 | 0.0776 | 0.9584 | 0.9995 | 0.0840 | 52.48 | 48.14 |
| 13 | 0.1216 | 0.6628 | 1.1097 | 0.0385 | 49.81 | — |
| 14 | 0.1063 | 0.7602 | 1.0923 | 0.0441 | 49.79 | — |
| 15 | 0.1422 | 0.7089 | 1.1061 | 0.0450 | 49.07 | — |
| 16 | 0.1202 | 0.6286 | 1.3126 | 0.0307 | 38.63 | — |
| 17 | 0.0978 | 0.7103 | 1.0463 | 0.0561 | 42.86 | — |
| 18 | 0.1031 | 0.6036 | 1.0741 | 0.0324 | 33.82 | — |
| 19 | 0.2271 | 0.4740 | 1.2740 | 0.0010 | 45.98 | — |
| 20 | 0.2773 | 0.4896 | 1.3063 | 0.0040 | 44.89 | — |
| 21 | 0.1164 | 0.9895 | 0.9603 | 0.1321 | 38.20 | — |
| 22 | 0.0907 | 0.7507 | 1.0486 | 0.0471 | 36.20 | — |
| 23 | 0.0575 | 0.9921 | 0.9591 | 0.0871 | 45.21 | — |
| 24 | 0.0467 | 0.9846 | 0.9763 | 0.0681 | 35.78 | — |
| 25 | 0.1103 | 0.6108 | 1.0783 | 0.0294 | 32.44 | — |
| 26 | 0.0875 | 0.7744 | 1.0350 | 0.0322 | 35.96 | — |
| 27 | 0.0480 | 0.9920 | 1.0089 | 0.632 | 45 | — |
| 28 | 0.0825 | 0.6940 | 1.0565 | 0.0351 | 35.89 | — |
| 29 | 0.0896 | 0.7376 | 1.0131 | 0.0925 | 39.58 | — |
| 30 | 0.0869 | 0.5640 | 1.0256 | 0.0895 | 38 | — |
| 31 | 0.0998 | 0.9802 | 0.9940 | 0.0828 | 51.23 | 57.23 |
| 32 | 0.1518 | 0.8998 | 0.9856 | 0.0956 | 54 | 58 |
| 33 | 0.1239 | 0.7990 | 0.8854 | 0.0897 | 52 | 55 |

TABLE 2 showing $T_{50}$, $T_{60}$, $T_{70}$, $T_{80}$ and $T_{90}$ values for different formulations.

| Example | $T_{50}$ | $T_{60}$ | $T_{70}$ | $T_{80}$ | $T_{90}$ |
|---|---|---|---|---|---|
| 1 | 5.24 | 6.38 | 7.42 | 9.61 | 11.14 |
| 2 | 6.29 | 7.27 | 8.49 | 9.78 | 10.91 |
| 3 | 4.06 | 5.13 | 6.28 | 7.64 | 10.52 |
| 4 | 4.20 | 5.31 | 6.39 | 7.75 | 10.46 |
| 5 | 8.88 | 10.74 | 14.65 | 20.85 | 22.91 |
| 6 | 12.83 | 15.87 | 19 | 22.213 | — |
| 7 | 10.75 | 13.912 | 17.302 | 20.893 | — |
| 8 | 9.80 | 11.7 | 14.93 | 22.61 | — |
| 9 | 6.14 | 7.72 | 9.95 | 14.23 | 19.07 |
| 10 | 4.65 | 5.96 | 7.46 | 9.39 | 11.2 |
| 11 | 6.37 | 7.64 | 9.47 | 11.6 | 18.84 |
| 12 | 6.84 | 7.81 | 8.99 | 16.35 | 16.35 |
| 13 | 6.26 | 7.5 | 9.83 | 18.53 | 18.53 |
| 14 | 6.46 | 7.62 | 9.07 | 11.81 | 18.53 |
| 15 | 5.87 | 7.25 | 8.6 | 10.1 | 14.39 |
| 16 | 7.9 | 9.95 | 13.27 | 20.34 | 24 |
| 17 | 7.38 | 10.17 | 14 | 22 | — |
| 18 | 9.81 | 13.96 | 18.96 | 22.62 | — |
| 19 | 5.22 | 6.84 | 8.85 | 10.98 | 14.59 |
| 20 | 4.48 | 5.91 | 6.93 | 8.38 | 10.92 |
| 21 | 4.84 | 5.57 | 6.71 | 8.5 | 10.78 |
| 22 | 8.8 | 13.12 | 18.71 | 22.12 | — |
| 23 | 8.88 | 10.45 | 11.37 | 17.17 | 21.56 |
| 24 | 9.79 | 1.69 | 15.57 | 19.51 | 23.12 |
| 25 | 10.73 | 16.02 | 21.1 | 24 | — |
| 26 | 9.03 | 14.68 | 19.26 | 22.14 | — |
| 27 | 8.8 | 10.64 | 13.68 | 20.7 | — |
| Glytop SR (5 mg) | 5.73 | 7.41 | 8.98 | 10.66 | 13.77 |
| Glucotrol XL (5 mg) | 5.41 | 7.63 | 9.23 | 10.23 | 12.68 |
| 28 | 13.278 | 17.35 | 21.74 | — | — |
| 29 | 8.719 | 11.025 | 13.444 | 15.964 | 18.577 |
| 30 | 7.314 | 9.586 | 10.289 | 11.236 | 12.356 |

Table 2 showing $T_{50}$, $T_{60}$, $T_{70}$, $T_{80}$ and $T_{90}$ values for different formulations, where
$T_{50}$ - Time in (hr) when 50% of the drug is released
$T_{60}$ - Time in (hr) when 60% of the drug is released
$T_{70}$ - Time in (hr) when 70% of the drug is released
$T_{80}$ - Time in (hr) when 80% of the drug is released
$T_{90}$ - Time in (hr) when 90% of the drug is released

TABLE 3

Showing the force of detachment of various formulations prepared according to the examples

| Example No. | Molecular wt. of the polymer | Polymer concentration (%) | Force of detachment (dynes/cm$^2$) |
|---|---|---|---|
| 1 | 4000,000 | 10 | 4000 |
| 2 | 4000,000 | 20 | 4500 |
| 5 | 4000,000 | 40 | 6000 |
| 6 | 4000,000 | 60 | 7000 |
| 7 | 4000,000 | 94 | 12000 |
| 10 | 7000,000 | 20 | 6000 |
| 11 | 7000,000 | 40 | 8000 |
| 12 | 7000,000 | 60 | 12500 |

What is claimed is:

1. A composition with an oral controlled release system useful for reducing serum glucose levels, said composition comprising:
   sulphonylurea at a concentration ranging from 5 to 20% by weight,
   polyethylene oxide polymer having a molecular weight of from 4 million to 8 million at a concentration ranging from 5 to 18% by weight,
   lubricant at a concentration ranging from 1 to 3% by weight, and
   dicalcium phosphate at a concentration of more than 50% by weight.

2. A composition as claimed in claim 1, wherein the lubricant is selected from the group consisting of magnesium stearate, and stearic acid.

3. A composition as claimed in claim 1, wherein said sulphonylurea is an antidiabetic drug.

4. A composition as claimed in claim 1, wherein said polyethylene oxide is a hydrophilic and water swellable polymer.

5. A composition as claimed in claim 1, wherein the composition is in a form of a tablet.

6. A composition as claimed in claim 1, wherein the sulphonylurea is released by erosion of the polyethylene oxide polymer.

7. A composition as claimed in claim 1, wherein the polyethylene oxide polymer erodes at a constant rate.

8. A method of treating hyperglycemia in a subject in need thereof using the composition of claim 1, said method comprising administering the composition of claim 1 on a daily basis.

9. A method as claimed in claim 8, wherein the composition is effective for a time duration of about 24 hours.

10. A method as claimed in claim 8, wherein the sulphonylurea is released by erosion of the polyethylene oxide polymer.

11. A method as claimed in claim 8, wherein the polyethylene oxide polymer erodes at a constant rate.

* * * * *